United States Patent
Haupt et al.

(10) Patent No.: US 8,362,010 B2
(45) Date of Patent: *Jan. 29, 2013

(54) BENZENESULFONANILIDE COMPOUNDS SUITABLE FOR TREATING DISORDERS THAT RESPOND TO MODULATION OF THE SEROTONIN 5-HT$_6$ RECEPTOR

(75) Inventors: Andreas Haupt, Ludwigshafen (DE); Frauke Pohlki, Ludwigshafen (DE); Karla Drescher, Ludwigshafen (DE); Karsten Wicke, Ludwigshafen (DE); Liliane Unger, Ludwigshafen (DE); Ana-Lucia Relo, Ludwigshafen (DE); Anton Bespalov, Ludwigshafen (DE); Barbara Vogg, Ludwigshafen (DE); Gisela Backfisch, Ludwigshafen (DE); Juergen Delzer, Ludwigshafen (DE); Min Zhang, Abbott Park, IL (US)

(73) Assignees: Abbott GmbH & Co. KG, Wiesbaden (DE); Abbott Laboratories, Abbott Park, IL (US)

( * ) Notice: Subject to any disclaimer, the term of this patent is extended or adjusted under 35 U.S.C. 154(b) by 285 days.

This patent is subject to a terminal disclaimer.

(21) Appl. No.: 12/769,878

(22) Filed: Apr. 29, 2010

(65) Prior Publication Data
US 2010/0292220 A1 Nov. 18, 2010

Related U.S. Application Data

(60) Provisional application No. 61/174,051, filed on Apr. 30, 2009.

(51) Int. Cl.
| | |
|---|---|
| *A61P 3/04* | (2006.01) |
| *A61P 25/18* | (2006.01) |
| *A61K 31/551* | (2006.01) |
| *C07D 243/08* | (2006.01) |

(52) U.S. Cl. .......................... 514/218; 540/575
(58) Field of Classification Search .................. 514/218; 540/575
See application file for complete search history.

(56) References Cited

U.S. PATENT DOCUMENTS
2003/0069233 A1  4/2003  Bromidge et al.

FOREIGN PATENT DOCUMENTS
| | | |
|---|---|---|
| WO | 9827081 | 6/1998 |
| WO | 9902502 | 1/1999 |
| WO | 0012073 | 3/2000 |
| WO | 0012623 | 3/2000 |
| WO | 0208179 | 1/2002 |
| WO | 02092585 | 11/2002 |
| WO | 2006010629 | 2/2006 |
| WO | 2008087123 | 7/2008 |

OTHER PUBLICATIONS

A. Meneses, Drug News Perspect 14(7) (2001) pp. 396-400.
J. Pharmacol. Sci. vol. 101, (Suppl. 1), 2006, p. 124.

Primary Examiner — Brenda Coleman
(74) Attorney, Agent, or Firm — Lisa V. Mueller; Michael Best & Friedrich LLP

(57) ABSTRACT

The present invention relates to novel benzenesulfonanilide compounds of the formulae I and I' and physiologically tolerated acid addition salts and the N-oxides thereof. The compounds possess valuable therapeutic properties and are particularly suitable, for treating diseases that respond to modulation of the serotonin 5-HT$_6$ receptor.

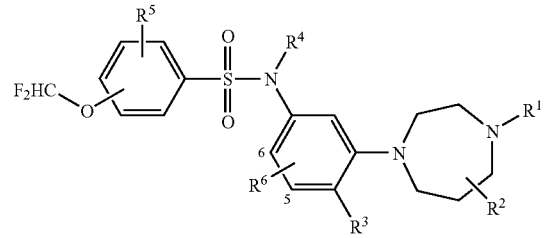

(I)

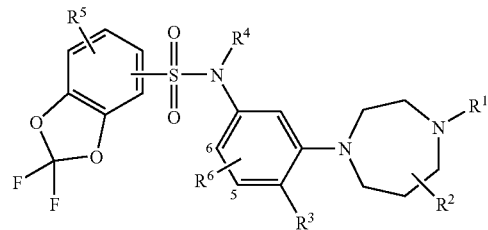

(I')

wherein
$R^1$ is hydrogen or methyl;
$R^2$ is hydrogen or methyl and is positioned vicinal to the radical $R^1$;
$R^3$ hydrogen, $C_1$-$C_3$ alkyl, halogen, $C_1$-$C_3$ alkoxy, fluorinated $C_1$-$C_3$ alkyl or fluorinated $C_1$-$C_3$ alkoxy;
$R^4$ is hydrogen, $C_1$-$C_4$ alkyl, $C_3$-$C_4$ cycloalkyl, $C_3$-$C_4$ cycloalkylmethyl or fluorinated $C_1$-$C_4$ alkyl;
$R^5$ is hydrogen, fluorine, chlorine, $C_1$-$C_4$ alkyl, fluorinated $C_1$-$C_4$ alkyl, $C_1$-$C_4$ alkoxy or fluorinated $C_1$-$C_4$ alkoxy; and
$R^6$ is hydrogen, fluorine or chlorine.

23 Claims, No Drawings

BENZENESULFONANILIDE COMPOUNDS SUITABLE FOR TREATING DISORDERS THAT RESPOND TO MODULATION OF THE SEROTONIN 5-HT$_6$ RECEPTOR

CROSS-REFERENCE TO RELATED APPLICATIONS

This claims priority to U.S. Provisional Patent Application Ser. No. 61/174,051, filed Apr. 30, 2009, the contents of which are hereby incorporated by reference.

BACKGROUND OF THE INVENTION

The present invention relates to novel benzenesulfonanilide compounds, pharmaceutical compositions containing them, and their use in therapy. The compounds possess valuable therapeutic properties and are particularly suitable for treating diseases that respond to modulation of the serotonin 5-HT$_6$ receptor.

Serotonin (5-hydroxytryptamine, 5-HT), a monoamine neurotransmitter and local hormone, is formed by the hydroxylation and decarboxylation of tryptophan. The greatest concentration is found in the enterochromaffin cells of the gastrointestinal tract, the remainder being predominantly present in platelets and in the Central Nervous System (CNS). 5-HT is implicated in a vast array of physiological and pathophysiological pathways. In the periphery, it contracts a number of smooth muscles and induces endothelium-dependent vasodilation. In the CNS, it is believed to be involved in a wide range of functions, including the control of appetite, mood, anxiety, hallucinations, sleep, vomiting and pain perception.

Neurons that secrete 5-HT are termed serotonergic. The function of 5-HT is exerted upon its interaction with specific (serotonergic) neurons. Until now, seven types of 5-HT receptors have been identified: 5-HT$_1$ (with subtypes 5-HT$_{1A}$, 5-HT$_{1B}$, 5-HT$_{1D}$, 5-HT$_{1E}$ and 5-HT$_{1F}$), 5-HT$_2$ (with subtypes 5-HT$_{2A}$, 5-HT$_{2B}$ and 5-HT$_{2C}$), 5-HT$_3$, 5-HT$_4$, 5-HT$_5$ (with subtypes 5-HT$_{5A}$ and 5-HT$_{5B}$), 5-HT$_6$ and 5-HT$_7$. Most of these receptors are coupled to G-proteins that affect the activities of either adenylate cyclase or phospholipase Cγ.

The human 5-HT$_6$ receptors are positively coupled to adenylyl cyclase. They are distributed throughout the limbic, striatal and cortical regions of the brain and show a high affinity to antipsychotics.

The modulation of the 5-HT$_6$ receptor by suitable substances is expected to improve certain disorders including cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, addiction diseases and obesity (see e.g. A. Meneses, Drug News Perspect 14(7) (2001) pp. 396-400 and literature cited therein; J. Pharmacol. Sci. Vol. 101 (Suppl. 1), 2006, p. 124. Modulators of the 5HT$_6$-receptor such as PRX-07034 (Epix Pharmaceuticals) have been found in preclinical and clinical studies to be particular useful in the treatment of cognitive dysfunctions, in particular associated with Alzheimer's disease or schizophrenia or in the treatment of obesity (see e.g. http://www.epixpharma.com/products/prx-07034.asp).

WO 98/027081, WO 99/02502, WO 00/12623, WO 00/12073, US 2003/0069233, WO 02/08179, WO 02/92585 and WO 2006/010629 disclose certain benzenesulfonanilide compounds having 5HT$_6$ receptor antagonist activity and suggest the use of these compounds for the treatment of medical disorders which are susceptible to the treatment with 5HT$_6$ receptor antagonists such as certain CNS disorders, drug abuse, ADHD, obesity and type II diabetes. WO 2008087123 suggests compounds having 5HT$_6$ receptor antagonist activity for preventing relapse into addiction.

However, there is still an ongoing need for providing compounds having high affinity for the 5-HT$_6$ receptor and which show high selectivity to this receptor. In particular the compounds should have low affinity to adrenergic receptors, such as α$_1$-adrenergic receptor, histamine receptors, such as H$_1$-receptor, and dopaminergic receptors, such as D$_2$-receptor, in order to avoid or reduce considerable side effects associated with modulation of these receptors, such as postural hypotension, reflex tachycardia, potentiation of the antihypertensive effect of prazosin, terazosin, doxazosin and labetalol or dizziness associated to the blockade of the α$_1$-adrenergic receptor, weight gain, sedation, drowsiness or potentiation of central depressant drugs associated to the blockade of the H$_1$-receptor, or extrapyramidal movement disorder, such as dystonia, parkinsonism, akathisia, tardive dyskinesia or rabbit syndrome, or endocrine effects, such as prolactin elevation (galactorrhea, gynecomastia, menstruyl changes, sexual dysfunction in males), associated to the blockade of the D$_2$-receptor.

It is one object of the present invention to provide compounds which have a high affinity for the 5-HT$_6$ receptor. It is a further object of the present invention to provide compounds which selectively bind to the 5-HT$_6$ receptor.

The compounds should also have good pharmacological profile, e.g. a good bioavailability and/or a good metabolic stability.

SUMMARY OF THE INVENTION

It has now been found that the benzenesulfonamide compounds of the formulae (I) and (I') as defined herein, their physiologically tolerated acid addition salts and the N-oxides thereof exhibit to a surprising and unexpected degree, selective binding to the 5-HT$_6$ receptor. Therefore, the present invention relates to the compounds of formulae (I) and (I'), to their physiologically tolerated acid addition salts, to the N-oxides of the formula (I) or (I') and to the physiologically tolerated acid addition salts of said N-oxides:

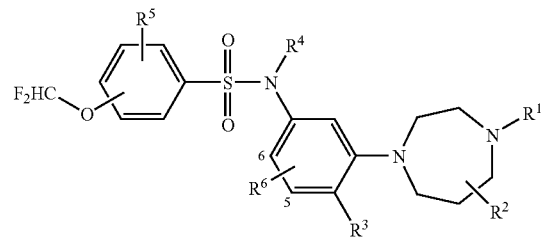

(I)

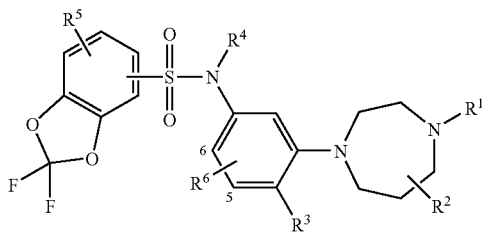

(I')

wherein
R¹ is hydrogen or methyl;
R² is hydrogen or methyl;
R³ hydrogen, $C_1$-$C_3$ alkyl, halogen, $C_1$-$C_3$ alkoxy, fluorinated $C_1$-$C_3$ alkyl or fluorinated $C_1$-$C_3$ alkoxy;
R⁴ is hydrogen, $C_1$-$C_4$ alkyl, $C_3$-$C_4$ cycloalkyl, $C_3$-$C_4$ cycloalkylmethyl or fluorinated $C_1$-$C_4$ alkyl;
R⁵ is hydrogen, fluorine, chlorine, $C_1$-$C_4$ alkyl, fluorinated $C_1$-$C_4$ alkyl, $C_1$-$C_4$ alkoxy or fluorinated $C_1$-$C_4$ alkoxy; and
R⁶ is hydrogen, fluorine or chlorine;
wherein R² is positioned vicinal to the radical R¹.

In this connection the term "positioned vicinal to the radical R¹" means that R² is linked to a carbon atom adjacent to the nitrogen atom to which R¹ is attached.

The present invention also relates to a pharmaceutical composition which comprises at least one benzenesulfonanilide compound of the formulae (I) or (I') and/or at least one physiologically tolerated acid addition salt of (I) or (I') and/or at least one N-oxide of (I) or (I'), where appropriate together with physiologically acceptable carriers and/or auxiliary substances.

The present invention further relates to the use of a benzenesulfonanilide compound of the formulae (I) or (I') and/or physiologically tolerated acid addition salts thereof and/or at least one N-oxide of (I) or (I') or a salt thereof, for preparing a pharmaceutical composition, optionally together with at least one physiologically acceptable carrier or auxiliary substance.

The compounds are selective 5-HT₆ receptor ligands. Thus the compounds are particularly suitable for the treatment of disorders of the central nervous system, addiction diseases or obesity, as these disorders and diseases are likely to respond to influencing by 5-HT₆ receptor ligands. Therefore the present invention also provides a method for treating disorders in mammals, said method comprising administering an effective amount of at least one compound of the formula (I) or (I') and/or at least one physiologically tolerated acid addition salt of (I) or (I') and/or at least one N-oxide of (I) or (I') to a subject in need thereof.

DETAILED DESCRIPTION OF THE INVENTION

The diseases which are susceptible to treatment with a benzenesulfonanilide compound of the formulae (I) and (I') include, e.g., disorders and diseases of the central nervous system, in particular cognitive dysfunctions, such as a deficit in memory, cognition and learning, in particular associated with Alzheimer's disease, age-related cognitive decline and mild cognitive impairment, attention deficit disorder/hyperactivity syndrome (ADHD), personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, including hydrocephalus, drug addiction and obesity.

According to the invention, at least one benzenesulfonanilide compound of the general formulae (I) or (I'), an N-oxide of (I) or (I') or a salt thereof is used for treating the above mentioned diseases, disorders or medical indications. Provided the compounds of the formulae (I) or (I') of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formulae (I) or (I') and/or of their salts and/or their N-oxides.

It is likewise possible to use physiologically tolerated salts of the compounds of the formulae (I) or (I'), especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

It is likewise possible to use N-oxides of the compounds of the formulae (I) or (I'), if those compounds contain a basic nitrogen atom, such as the nitrogen atom of the piperazine moiety.

It is likewise possible to use the physiologically tolerated acid addition salts of said N-oxides.

The organic moieties mentioned in the above definitions of the variables are—like the term halogen—collective terms for individual listings of the individual group members. The prefix $C_n$-$C_m$ indicates in each case the possible number of carbon atoms in the group.

As used herein, $C_1$-$C_4$ alkyl is a straight-chain or branched alkyl group having 1, 2, 3 or 4 carbon atoms. Examples of such a group include methyl, ethyl, n-propyl, 1-methylethyl (isopropyl), n-butyl, 1-methylpropyl (=2-butyl), 2-methylpropyl (=isobutyl) and 1,1-dimethylethyl (=tert.-butyl). $C_1$-$C_3$ alkyl refers to a straight-chain or branched alkyl group as defined above having 1, 2 or 3 carbon atoms.

As used herein, fluorinated $C_1$-$C_2$ alkyl is a straight-chain alkyl group having for 2 carbon atoms, wherein at least one hydrogen atom, e.g. 1, 2, 3, 4 or 5 hydrogen atoms, are replaced by fluorine. Examples of such a group include fluoromethyl, difluoromethyl, trifluoromethyl, 2-fluoroethyl, 2,2-difluoroethyl, 2,2,2-trifluoroethyl, 1,1,2,2-tetrafluoroethyl and 1,1,2,2,2-pentafluoroethyl.

As used herein, fluorinated $C_1$-$C_4$ alkyl is a straight-chain or branched alkyl group having 1, 2, 3 or 4 carbon atoms, wherein at least one hydrogen atom, e.g. 1, 2, 3, 4, 5, 6 or 7 hydrogen atoms, are replaced by fluorine. Examples of such a group include fluoromethyl, difluoromethyl, trifluoromethyl, 2-fluoroethyl, 2,2-difluoroethyl, 2,2,2-trifluoroethyl, 1,1,2,2-tetrafluoroethyl, 1,1,2,2,2-pentafluoroethyl, 3-fluoropropyl, 3,3-difluoropropyl, 3,3,3-trifluoropropyl, 2,2,3,3-tetrafluoropropyl, 2,2,3,3,3-pentafluoropropyl, 1,1,2,2,3,3,3-heptafluoropropyl, 2-fluoro-1-methylethyl, 2,2-difluoro-1-methylethyl, 2,2,2-trifluoro-1-methylethyl, 2,2,2-trifluoro-1-(trifluoromethyl)ethyl etc.

As used herein, $C_1$-$C_4$ alkoxy is a straight-chain or branched alkyl group having 1, 2, 3 or 4, in particular 1 or 2 carbon atoms, which is bound to the remainder of the molecule via an oxygen atom. Examples of such a group are methoxy and ethoxy.

As used herein, fluorinated $C_1$-$C_4$ alkoxy is an alkoxy group as defined above, wherein at least one, e.g. 1, 2, 3, 4, 5, 6 or 7 hydrogen atoms are replaced by fluorine atoms. Examples of such a group are fluoromethoxy, difluoromethoxy, trifluoromethoxy, 2-fluoroethoxy, 2,2-difluoroethoxy, 2,2,2-trifluoroethoxy and 1,1,2,2-tetrafluoroethoxy.

As used herein, $C_3$-$C_4$ cycloalkyl is a cycloaliphatic radical having from 3 to 4 carbon atoms, i.e. cyclopropyl and cyclobutyl.

As used herein, $C_3$-$C_4$ cycloalkylmethyl is a methylene group that carries a cycloaliphatic radical having from 3 to 4 carbon atoms, i.e. $CH_2$-cyclopropyl (=$CH_2$-c-Pr) and $CH_2$-cyclobutyl (=$CH_2$-c-But).

In the formulae I and I', the integers "5" and "6" denominate positions of the benzene ring.

With respect to the compounds' capability of modulating the 5-$HT_6$ receptor, the variables $R^1$, $R^2$, $R^3$, $R^4$, $R^5$ and $R^6$ preferably have the following meanings which, when taken alone or in combination, represent particular embodiments of the compounds of the formula (I) or (I').

A first preferred embodiment of the invention relates to compounds of the formulae I and I', to their pharmacologically tolerated salts and to the N-oxides thereof, wherein $R^1$ is hydrogen.

Another preferred embodiment of the invention relates to compounds of the formulae I and I', to their pharmacologically tolerated salts and to the N-oxides thereof, wherein $R^1$ is methyl.

A preferred embodiment of the invention relates to compounds of the formulae I and I', to their pharmacologically tolerated salts and to the N-oxides thereof, wherein $R^2$ is hydrogen.

Another embodiment of the invention relates to compounds of the formulae I and I', wherein $R^2$ is methyl. In the compounds, wherein $R^2$ is methyl, the carbon atom that carries $R^2$ creates a center of chirality. Thus, a specific embodiment of the invention relates to compounds of the formula I, to their pharmacologically tolerated salts and to the N-oxides thereof, wherein $R^2$ is methyl and wherein the carbon atom that carries $R^2$ has S-configuration. Another specific embodiment of the invention relates to compounds of the formulae I and I', to their pharmacologically tolerated salts and to the N-oxides thereof, wherein $R^2$ is methyl and wherein the carbon atom that carries $R^2$ has R-configuration.

Likewise preferred are mixtures of compounds of the present invention, wherein the carbon atom that carries $R^2$ has S-configuration or R-configuration, respectively. These mixtures may contain equal amounts or non-equal amounts of the compound I, or equal amounts or non-equal amounts of the compound I', respectively, that have R-configuration with regard to the moiety CH—$R^2$ and of the compound I or I' that have S-configuration with regard to CH—$R^2$.

The term "enantiomerically pure" means that the mixture contains the respective compound in an enantiomeric excess of at least 80%, in particular at least 90% (ee).

Preference is given to compounds of the formulae I and I', to their pharmacologically tolerated salts and to the N-oxides thereof, wherein $R^3$ is $C_1$-$C_3$ alkoxy, fluorinated $C_1$-$C_3$ alkyl or fluorinated $C_1$-$C_3$ alkoxy, in particular methoxy, trifluoromethyl, difluoromethoxy or trifluoromethoxy, specifically methoxy. Likewise preference is given to compounds of the formulae I and I', to their pharmacologically tolerated salts and to the N-oxides thereof, wherein $R^3$ is hydrogen or halogen, in particular hydrogen or fluorine, specifically hydrogen.

Preference is also given to compounds of the formulae I and I', to their pharmacologically tolerated salts and to the N-oxides thereof, wherein $R^3$ is $C_1$-$C_3$ alkyl, in particular methyl, ethyl or n-propyl, specifically methyl.

Preference is given to compounds of the formulae I and I', to their pharmacologically tolerated salts and to the N-oxides thereof, wherein $R^4$ is hydrogen, $C_1$-$C_4$ alkyl, cyclopropyl or cyclopropylmethyl. More preference is given to compounds of the present invention, wherein $R^4$ is hydrogen, methyl, ethyl, n-propyl, isopropyl, cyclopropyl or cyclopropylmethyl, in particular hydrogen, methyl, ethyl or n-propyl, and specifically hydrogen.

Preference is also given to compounds of the formulae I and I', to their pharmacologically tolerated salts and to the N-oxides thereof, wherein $R^5$ is hydrogen, fluorine, $C_1$-$C_4$ alkyl, fluorinated $C_1$-$C_4$ alkyl, $C_1$-$C_4$ alkoxy or fluorinated $C_1$-$C_4$ alkoxy. $R^5$ is preferably selected from the group consisting of hydrogen, fluorine, methyl, ethyl, trifluoromethyl, methoxy, ethoxy, difluoromethoxy and trifluoromethoxy and more preferably from hydrogen, methyl, methoxy and difluoromethoxy. In a particular preferred embodiment of the invention, $R^5$ is hydrogen. In another particular preferred embodiment of the invention, $R^5$ is selected from fluorine, methyl, trifluoromethyl, methoxy, difluoromethoxy and trifluoromethoxy and more preferably from methyl, methoxy and difluoromethoxy. Likewise, preference is given to compounds of the formulae I and I', to their pharmacologically tolerated salts and to the N-oxides thereof, wherein $R^5$ is chlorine.

$R^6$ is preferably selected from the group consisting of hydrogen and fluorine. In a particular preferred embodiment of the invention, $R^6$ is hydrogen. In another particular preferred embodiment of the invention $R^6$ is different from hydrogen, in particular fluorine. If $R^6$ is different from hydrogen it is preferably located in the 5- or 6-position of the benzene ring.

Preference is also given to those compounds of the formula I or I', to their pharmacologically tolerated salts and to the N-oxides thereof, wherein $R^3$ is methyl or methoxy and $R^6$ is hydrogen, or $R^3$ is methyl or methoxy and $R^6$ is fluorine being located in the 5- or 6-position of the benzene ring, or both $R^3$ and $R^6$ are hydrogen or $R^3$ is hydrogen and $R^6$ is fluorine being located in the 5- or 6-position of the benzene ring.

According to a particular embodiment, $R^5$ and $R^6$ are hydrogen, $R^3$ is selected from the group consisting of $C_1$-$C_2$ alkoxy (e.g. methoxy) and fluorinated $C_1$-$C_2$ alkoxy (e.g. difluoromethoxy) and $R^4$ is selected from the group consisting of hydrogen and $C_1$-$C_3$ alkyl (e.g. methyl, ethyl, n-propyl, isopropyl).

Preference is also given to those compounds of the formulae I and I', to their pharmacologically tolerated salts and to the N-oxides thereof, wherein one or more of the following provisos a), b), c) or d) are met:

a) $R^5$ is selected from the group consisting of fluorine, $C_1$-$C_2$ alkyl, fluorinated $C_1$-$C_2$ alkyl, $C_1$-$C_2$ alkoxy and fluorinated $C_1$-$C_2$ alkoxy, in particular from the group consisting of fluorine, methyl, trifluoromethyl, difluoromethoxy and methoxy;

b) $R^6$ is fluorine or chlorine, which is preferably located in 5- or 6-position of the benzene ring;
c) $R^3$ is hydrogen or fluorine, in particular hydrogen; and/or
d) $R^4$ is $C_3$-$C_4$-alkyl or fluorinated $C_1$-$C_4$-alkyl, in particular n-propyl, isopropyl or trifluoromethyl.

A particular preferred embodiment 1a of the invention relates to compounds of the formula I, to their pharmacologically tolerated salts and to the N-oxides thereof, wherein
$R^1$ is hydrogen;
$R^2$ is hydrogen;
$R^3$ is methoxy, difluoromethoxy or trifluoromethoxy, in particular methoxy; and
$R^4$ is hydrogen.

A further particular preferred embodiment 1b of the invention relates to compounds of the formula I, to their pharmacologically tolerated salts and to the N-oxides thereof, wherein
$R^1$ is hydrogen;
$R^2$ is hydrogen;
$R^3$ is methoxy, difluoromethoxy or trifluoromethoxy, in particular methoxy; and
$R^4$ is methyl.

A further particular preferred embodiment 1c of the invention relates to compounds of the formula I, to their pharmacologically tolerated salts and to the N-oxides thereof, wherein
$R^1$ is methyl;
$R^2$ is hydrogen;
$R^3$ is methoxy, difluoromethoxy or trifluoromethoxy, in particular methoxy; and
$R^4$ is hydrogen.

A further particular preferred embodiment 1d of the invention relates to compounds of the formula I, to their pharmacologically tolerated salts and to the N-oxides thereof, wherein
$R^1$ is methyl;
$R^2$ is hydrogen;
$R^3$ is methoxy, difluoromethoxy or trifluoromethoxy, in particular methoxy; and
$R^4$ is methyl.

A particular preferred embodiment 1e of the invention relates to compounds of the formula I, to their pharmacologically tolerated salts and to the N-oxides thereof, wherein
$R^1$ is hydrogen;
$R^2$ is hydrogen;
$R^3$ is hydrogen or fluorine, in particular hydrogen; and
$R^4$ is hydrogen.

A further particular preferred embodiment 1f of the invention relates to compounds of the formula I, to their pharmacologically tolerated salts and to the N-oxides thereof, wherein
$R^1$ is hydrogen;
$R^2$ is hydrogen;
$R^3$ is hydrogen or fluorine, in particular hydrogen; and
$R^4$ is methyl.

A further particular preferred embodiment 1g of the invention relates to compounds of the formula I, to their pharmacologically tolerated salts and to the N-oxides thereof, wherein
$R^1$ is methyl;
$R^2$ is hydrogen;
$R^3$ is hydrogen or fluorine, in particular hydrogen; and
$R^4$ is hydrogen.

A further particular preferred embodiment 1h of the invention relates to compounds of the formula I, to their pharmacologically tolerated salts and to the N-oxides thereof, wherein
$R^1$ is methyl;
$R^2$ is hydrogen;
$R^3$ is hydrogen or fluorine, in particular hydrogen; and
$R^4$ is methyl.

A particular preferred embodiment 1i of the invention relates to compounds of the formula I, to their pharmacologically tolerated salts and to the N-oxides thereof, wherein
$R^1$ is hydrogen;
$R^2$ is hydrogen;
$R^3$ is methyl; and
$R^4$ is hydrogen.

A further particular preferred embodiment 1j of the invention relates to compounds of the formula I, to their pharmacologically tolerated salts and to the N-oxides thereof, wherein
$R^1$ is hydrogen;
$R^2$ is hydrogen;
$R^3$ is methyl; and
$R^4$ is $C_1$-$C_3$ alkyl or cyclopropylmethyl, in particular methyl, ethyl or n-propyl.

A further particular preferred embodiment 1k of the invention relates to compounds of the formula I, to their pharmacologically tolerated salts and to the N-oxides thereof, wherein
$R^1$ is methyl;
$R^2$ is hydrogen;
$R^3$ is methyl; and
$R^4$ is hydrogen.

A further particular preferred embodiment 1l of the invention relates to compounds of the formula I, to their pharmacologically tolerated salts and to the N-oxides thereof, wherein
$R^1$ is methyl;
$R^2$ is hydrogen;
$R^3$ is methyl; and
$R^4$ is $C_1$-$C_3$ alkyl or cyclopropylmethyl, in particular methyl, ethyl or n-propyl.

Amongst the compounds of embodiments 1a, 1b, 1c, 1d, 1e, 1f, 1g, 1h, 1i, 1j, 1k and 1l, preference is given to those, where the radicals $R^5$ and $R^6$ in formula I are both hydrogen.

Amongst the compounds of embodiments 1a, 1b, 1c, 1d, 1e, 1f, 1g, 1h, 1i, 1j, 1k and 1l, likewise preference is given to those, where the radical $R^5$ in formula I is hydrogen and where the radical $R^6$ in formula I is fluorine, which is located in the 5-position or in the 6-position of the benzene ring.

Amongst the compounds of embodiments 1a, 1b, 1c, 1d, 1e, 1f, 1g, 1h, 1i, 1j, 1k and 1l, likewise preference is given to those, where the radical $R^5$ in formula I is methyl and where the radical $R^6$ in formula I is hydrogen.

Amongst the compounds of embodiments 1a, 1b, 1c, 1d, 1e, 1f, 1g, 1h, 1i, 1j, 1k and 1l, likewise preference is given to those, where the radical $R^5$ in formula I is methoxy and where the radical $R^6$ in formula I is hydrogen.

Amongst the compounds of embodiments 1a, 1b, 1c, 1d, 1e, 1f, 1g, 1h, 1i, 1j, 1k and 1l, likewise preference is given to those, where the radical $R^5$ in formula I is methyl and where the radical $R^6$ in formula I is fluorine, which is located in the 5-position or in the 6-position of the benzene ring.

Amongst the compounds of embodiments 1a, 1b, 1c, 1d, 1e, 1f, 1g, 1h, 1i, 1j, 1k and 1l, likewise preference is given to those, where the radical $R^5$ in formula I is methoxy and where the radical $R^6$ in formula I is fluorine, which is located in the 5-position or in the 6-position of the benzene ring.

Amongst the compounds of embodiments 1a, 1b, 1c, 1d, 1e, 1f, 1g, 1h, 1i, 1j, 1k and 1l, likewise preference is given to those, where the radical $R^5$ in formula I is difluoromethoxy and where the radical $R^6$ in formula I is hydrogen.

Amongst the compounds of embodiments 1a, 1b, 1c, 1d, 1e, 1f, 1g, 1h, 1i, 1j, 1k and 1l, likewise preference is given to those, where the radical $R^5$ in formula I is difluoromethoxy and where the radical $R^6$ in formula I is fluorine, which is located in the 5-position or in the 6-position of the benzene ring.

A particular preferred embodiment 1'a of the invention relates to compounds of the formula I', to their pharmacologically tolerated salts and to the N-oxides thereof, wherein
$R^1$ is hydrogen;
$R^2$ is hydrogen;
$R^3$ is methoxy, difluoromethoxy or trifluoromethoxy, in particular methoxy; and
$R^4$ is hydrogen.

A further particular preferred embodiment 1'b of the invention relates to compounds of the formula I', to their pharmacologically tolerated salts and to the N-oxides thereof, wherein
$R^1$ is hydrogen;
$R^2$ is methyl;
$R^3$ is methoxy, difluoromethoxy or trifluoromethoxy, in particular methoxy; and
$R^4$ is hydrogen.

A further particular preferred embodiment 1'c of the invention relates to compounds of the formula I', to their pharmacologically tolerated salts and to the N-oxides thereof, wherein
$R^1$ is hydrogen;
$R^2$ is hydrogen;
$R^3$ is methoxy, difluoromethoxy or trifluoromethoxy, in particular methoxy; and
$R^4$ is methyl.

A further particular preferred embodiment 1'd of the invention relates to compounds of the formula I', to their pharmacologically tolerated salts and to the N-oxides thereof, wherein
$R^1$ is hydrogen;
$R^2$ is methyl;
$R^3$ is methoxy, difluoromethoxy or trifluoromethoxy, in particular methoxy; and
$R^4$ is methyl.

A particular preferred embodiment 1'e of the invention relates to compounds of the formula I', to their pharmacologically tolerated salts and to the N-oxides thereof, wherein
$R^1$ is hydrogen;
$R^2$ is hydrogen;
$R^3$ is hydrogen or fluorine, in particular hydrogen; and
$R^4$ is hydrogen.

A further particular preferred embodiment 1'f of the invention relates to compounds of the formula I', to their pharmacologically tolerated salts and to the N-oxides thereof, wherein
$R^1$ is hydrogen;
$R^2$ is methyl;
$R^3$ is hydrogen or fluorine, in particular hydrogen; and
$R^4$ is hydrogen.

A further particular preferred embodiment 1'g of the invention relates to compounds of the formula I', to their pharmacologically tolerated salts and to the N-oxides thereof, wherein
$R^1$ is hydrogen;
$R^2$ is hydrogen;
$R^3$ is hydrogen or fluorine, in particular hydrogen; and
$R^4$ is methyl.

A further particular preferred embodiment 1'h of the invention relates to compounds of the formula I', to their pharmacologically tolerated salts and to the N-oxides thereof, wherein
$R^1$ is hydrogen;
$R^2$ is methyl;
$R^3$ is hydrogen or fluorine, in particular hydrogen; and
$R^4$ is methyl.

A particular preferred embodiment 1'i of the invention relates to compounds of the formula I', to their pharmacologically tolerated salts and to the N-oxides thereof, wherein
$R^1$ is hydrogen;
$R^2$ is hydrogen;
$R^3$ is methyl; and
$R^4$ is hydrogen.

A further particular preferred embodiment 1'j of the invention relates to compounds of the formula I', to their pharmacologically tolerated salts and to the N-oxides thereof, wherein
$R^1$ is hydrogen;
$R^2$ is methyl;
$R^3$ is methyl; and
$R^4$ is hydrogen.

A further particular preferred embodiment 1'k of the invention relates to compounds of the formula I', to their pharmacologically tolerated salts and to the N-oxides thereof, wherein
$R^1$ is hydrogen;
$R^2$ is hydrogen;
$R^3$ is methyl; and
$R^4$ is $C_1$-$C_3$ alkyl or cyclopropylmethyl, in particular methyl, ethyl or n-propyl.

A further particular preferred embodiment 1'l of the invention relates to compounds of the formula I', to their pharmacologically tolerated salts and to the N-oxides thereof, wherein
$R^1$ is hydrogen;
$R^2$ is methyl;
$R^3$ is methyl; and
$R^4$ is $C_1$-$C_3$ alkyl or cyclopropylmethyl, in particular methyl, ethyl or n-propyl.

Amongst the compounds of embodiments 1'a, 1'b, 1'c, 1'd, 1'e, 1'f, 1'g, 1'h, 1'i, 1'k and 1'l, preference is given to those, where the radicals $R^5$ and $R^6$ in formula I are both hydrogen.

Amongst the compounds of embodiments 1'a, 1'b, 1'c, 1'd, 1'e, 1'f, 1'g, 1'h, 1'k and 1'l, likewise preference is given to those, where the radical $R^5$ in formula I is hydrogen and where the radical $R^6$ in formula I is fluorine, which is located in the 5-position or in the 6-position of the benzene ring.

Amongst the compounds of the formula I, in particular amongst the compounds of embodiments 1a, 1b, 1c, 1d, 1e, 1f, 1g, 1h, 1i, 1j, 1k and 1l, particular preference is given to those, wherein the $OCHF_2$-radical is located on the benzene ring in the meta-position with respect to the sulfonyl group. Amongst these compounds, particular preference is given to those compounds of the formula I, wherein $R^5$ is hydrogen. Amongst these compounds, likewise preference is given to those compounds of the formula I, wherein $R^5$ is different from hydrogen and in particular selected from fluorine, methyl, trifluoromethyl, methoxy, difluoromethoxy and trifluoromethoxy and more preferably from methyl, methoxy and difluoromethoxy, and located in the para-position, with respect to the sulfonyl group, or in the para-position, with respect to the $OCHF_2$-radical.

Amongst the compounds of the formula I, in particular amongst the compounds of embodiments 1a, 1b, 1c, 1d, 1e, 1f, 1g, 1h, 1i, 1j, 1k and 1l, likewise preference is given to those, wherein the OCHF$_2$-radical is located on the benzene ring in the ortho-position with respect to the sulfonyl group. Amongst these compounds, particular preference is given to those compounds of the formula I, wherein R$^5$ is hydrogen. Amongst these compounds, likewise preference is given to those compounds of the formula I, wherein R$^5$ is different from hydrogen and in particular selected from fluorine, methyl, trifluoromethyl, methoxy, difluoromethoxy and trifluoromethoxy and more preferably from methyl, methoxy and difluoromethoxy, and located in the para-position, with respect to the sulfonyl group, or in the para-position, with respect to the OCHF$_2$-radical.

Amongst the compounds of the formula I, in particular amongst the compounds of embodiments 1a, 1b, 1c, 1d, 1e, 1f, 1g, 1h, 1i, 1j, 1k and 1l, likewise preference is given to those, wherein the OCHF$_2$-radical is located on the benzene ring in the para-position with respect to the sulfonyl group. Amongst these compounds, particular preference is given to those compounds of the formula I, wherein R$^5$ is hydrogen. Amongst these compounds, likewise preference is given to those compounds of the formula I, wherein R$^5$ is different from hydrogen and in particular selected from fluorine, methyl, trifluoromethyl, methoxy, difluoromethoxy and trifluoromethoxy and more preferably from methyl, methoxy and difluoromethoxy, and located in the meta-position, with respect to the sulfonyl group.

Amongst the compounds of the formula I', in particular amongst the compounds of embodiments 1'a, 1'b, 1'c, 1'd, 1'e, 1'f, 1'g, 1'h, 1'l, 1'j, 1'k and 1'l, particular preference is given to those, wherein the sulfonyl group is attached to the benzene ring in the α-position with respect to the 1,3-dioxole ring. Amongst these compounds, particular preference is given to those compounds of the formula I', wherein R$^5$ is hydrogen.

Amongst the compounds of the formula I', in particular amongst the compounds of embodiments 1'a, 1'b, 1'c, 1'd, 1'e, 1'f, 1'g, 1'h, 1'i, 1'j, 1'k and 1'l, particular preference is given to those, wherein the sulfonyl group is attached to the benzene ring in the β-position with respect to the 1,3-dioxole ring. Amongst these compounds, particular preference is given to those compounds of the formula I', wherein R$^5$ is hydrogen.

A particular preferred embodiment of the invention relates to compounds of the formulae I and I', to their pharmacologically tolerated salts and to the N-oxides thereof, wherein
R$^1$ is hydrogen or methyl;
R$^2$ is hydrogen or methyl, in particular hydrogen;
R$^3$ hydrogen, C$_1$-C$_2$ alkyl, fluorine, C$_1$-C$_2$ alkoxy, fluorinated C$_1$-C$_2$ alkyl or fluorinated C$_1$-C$_2$ alkoxy, preferably hydrogen, methyl, methoxy, trifluoromethyl, difluoromethoxy or trifluoromethoxy, in particular hydrogen, methyl or methoxy;
R$^4$ is hydrogen, methyl, ethyl, n-propyl, isopropyl, cyclopropyl or cyclopropylmethyl, in particular hydrogen, methyl or ethyl;
R$^5$ is hydrogen, fluorine, methyl, ethyl, trifluoromethyl, methoxy, ethoxy, difluoromethoxy or trifluoromethoxy, and more preferably hydrogen, methyl, methoxy, difluoromethoxy or trifluoromethoxy; and
R$^6$ is hydrogen or fluorine, which is located in the 5- or 6-position of the benzene ring, in particular hydrogen.

A further particular preferred embodiment of the invention relates to compounds of the formulae I and I', to their pharmacologically tolerated salts and to the N-oxides thereof, wherein
R$^1$ is hydrogen or methyl, in particular hydrogen;
R$^2$ is hydrogen;
R$^3$ hydrogen, fluorine, C$_1$-C$_2$ alkyl or C$_1$-C$_2$ alkoxy, in particular hydrogen, fluorine, methyl or methoxy, especially methyl or methoxy;
R$^4$ is hydrogen, methyl, ethyl, n-propyl, isopropyl, cyclopropyl or cycloproplymethyl, in particular hydrogen, methyl or ethyl;
R$^5$ is hydrogen, methyl or methoxy, in particular hydrogen; and
R$^6$ is hydrogen.

A further particular preferred embodiment of the invention relates to compounds of the formulae I and I', to their pharmacologically tolerated salts and to the N-oxides thereof, wherein
R$^1$ is hydrogen;
R$^2$ is hydrogen;
R$^3$ C$_1$-C$_2$ alkyl or C$_1$-C$_2$ alkoxy, in particular methyl or methoxy;
R$^4$ is hydrogen, methyl, ethyl or n-propyl, in particular hydrogen or methyl;
R$^5$ is hydrogen; and
R$^6$ is hydrogen.

Preferred compounds according to the present invention are the compounds of the formula I, their pharmacologically tolerated salts and the N-oxides thereof, wherein R$^2$ and R$^6$ are hydrogen and R$^1$, R$^3$, R$^4$, R$^5$ and the position of the moiety OCHF$_2$ on the benzene ring with respect to the sulfonyl group are as defined above. These compounds are hereinafter referred to as compounds of the formula I-1. Examples are given in the following table A:

TABLE A

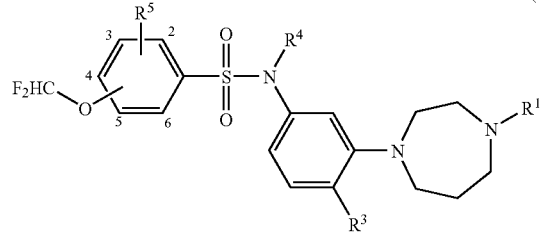

(I-1)

| No. | R$^1$ | R$^3$ | R$^4$ | position of OCHF$_2$ * | R$^5$ * |
|---|---|---|---|---|---|
| 1. | H | CH$_3$ | H | 2 | H |
| 2. | H | CH$_3$ | H | 3 | H |
| 3. | H | CH$_3$ | H | 4 | H |
| 4. | H | CH$_3$ | H | 3 | 6-OCH$_3$ |
| 5. | H | CH$_3$ | H | 2 | 4-OCH$_3$ |
| 6. | H | CH$_3$ | H | 3 | 4-OCH$_3$ |
| 7. | H | CH$_3$ | H | 3 | 6-CH$_3$ |
| 8. | H | CH$_3$ | H | 2 | 4-CH$_3$ |
| 9. | H | CH$_3$ | H | 3 | 4-CH$_3$ |
| 10. | CH$_3$ | CH$_3$ | H | 2 | H |
| 11. | CH$_3$ | CH$_3$ | H | 3 | H |
| 12. | CH$_3$ | CH$_3$ | H | 4 | H |
| 13. | CH$_3$ | CH$_3$ | H | 3 | 6-OCH$_3$ |
| 14. | CH$_3$ | CH$_3$ | H | 2 | 4-OCH$_3$ |
| 15. | CH$_3$ | CH$_3$ | H | 3 | 4-OCH$_3$ |
| 16. | CH$_3$ | CH$_3$ | H | 3 | 6-CH$_3$ |
| 17. | CH$_3$ | CH$_3$ | H | 2 | 4-CH$_3$ |
| 18. | CH$_3$ | CH$_3$ | H | 3 | 4-CH$_3$ |
| 19. | H | CH$_3$ | CH$_3$ | 2 | H |
| 20. | H | CH$_3$ | CH$_3$ | 3 | H |
| 21. | H | CH$_3$ | CH$_3$ | 4 | H |
| 22. | H | CH$_3$ | CH$_3$ | 3 | 6-OCH$_3$ |
| 23. | H | CH$_3$ | CH$_3$ | 2 | 4-OCH$_3$ |
| 24. | H | CH$_3$ | CH$_3$ | 3 | 4-OCH$_3$ |
| 25. | H | CH$_3$ | CH$_3$ | 3 | 6-CH$_3$ |
| 26. | H | CH$_3$ | CH$_3$ | 2 | 4-CH$_3$ |

TABLE A-continued

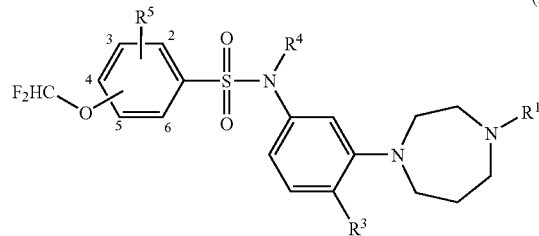

(I-1)

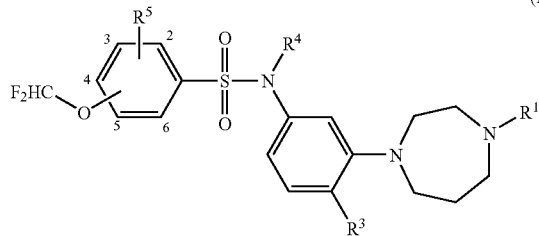

(I-1)

| No. | R¹ | R³ | R⁴ | position of OCHF₂ * | R⁵ * | No. | R¹ | R³ | R⁴ | position of OCHF₂ * | R⁵ * |
|---|---|---|---|---|---|---|---|---|---|---|---|
| 27. | H | CH₃ | CH₃ | 3 | 4-CH₃ | 91. | H | CH₃ | CH₂—c-Pr | 2 | H |
| 28. | CH₃ | CH₃ | CH₃ | 2 | H | 92. | H | CH₃ | CH₂—c-Pr | 3 | H |
| 29. | CH₃ | CH₃ | CH₃ | 3 | H | 93. | H | CH₃ | CH₂—c-Pr | 4 | H |
| 30. | CH₃ | CH₃ | CH₃ | 4 | H | 94. | H | CH₃ | CH₂—c-Pr | 3 | 6-OCH₃ |
| 31. | CH₃ | CH₃ | CH₃ | 3 | 6-OCH₃ | 95. | H | CH₃ | CH₂—c-Pr | 2 | 4-OCH₃ |
| 32. | CH₃ | CH₃ | CH₃ | 2 | 4-OCH₃ | 96. | H | CH₃ | CH₂—c-Pr | 3 | 4-OCH₃ |
| 33. | CH₃ | CH₃ | CH₃ | 3 | 4-OCH₃ | 97. | H | CH₃ | CH₂—c-Pr | 3 | 6-CH₃ |
| 34. | CH₃ | CH₃ | CH₃ | 3 | 6-CH₃ | 98. | H | CH₃ | CH₂—c-Pr | 2 | 4-CH₃ |
| 35. | CH₃ | CH₃ | CH₃ | 2 | 4-CH₃ | 99. | H | CH₃ | CH₂—c-Pr | 3 | 4-CH₃ |
| 36. | CH₃ | CH₃ | CH₃ | 3 | 4-CH₃ | 100. | CH₃ | CH₃ | CH₂—c-Pr | 2 | H |
| 37. | H | CH₃ | CH₂CH₃ | 2 | H | 101. | CH₃ | CH₃ | CH₂—c-Pr | 3 | H |
| 38. | H | CH₃ | CH₂CH₃ | 3 | H | 102. | CH₃ | CH₃ | CH₂—c-Pr | 4 | H |
| 39. | H | CH₃ | CH₂CH₃ | 4 | H | 103. | CH₃ | CH₃ | CH₂—c-Pr | 3 | 6-OCH₃ |
| 40. | H | CH₃ | CH₂CH₃ | 3 | 6-OCH₃ | 104. | CH₃ | CH₃ | CH₂—c-Pr | 2 | 4-OCH₃ |
| 41. | H | CH₃ | CH₂CH₃ | 2 | 4-OCH₃ | 105. | CH₃ | CH₃ | CH₂—c-Pr | 3 | 4-OCH₃ |
| 42. | H | CH₃ | CH₂CH₃ | 3 | 4-OCH₃ | 106. | CH₃ | CH₃ | CH₂—c-Pr | 3 | 6-CH₃ |
| 43. | H | CH₃ | CH₂CH₃ | 3 | 6-CH₃ | 107. | CH₃ | CH₃ | CH₂—c-Pr | 2 | 4-CH₃ |
| 44. | H | CH₃ | CH₂CH₃ | 2 | 4-CH₃ | 108. | CH₃ | CH₃ | CH₂—c-Pr | 3 | 4-CH₃ |
| 45. | H | CH₃ | CH₂CH₃ | 3 | 4-CH₃ | 109. | H | OCH₃ | H | 2 | H |
| 46. | CH₃ | CH₃ | CH₂CH₃ | 2 | H | 110. | H | OCH₃ | H | 3 | H |
| 47. | CH₃ | CH₃ | CH₂CH₃ | 3 | H | 111. | H | OCH₃ | H | 4 | H |
| 48. | CH₃ | CH₃ | CH₂CH₃ | 4 | H | 112. | H | OCH₃ | H | 3 | 6-OCH₃ |
| 49. | CH₃ | CH₃ | CH₂CH₃ | 3 | 6-OCH₃ | 113. | H | OCH₃ | H | 2 | 4-OCH₃ |
| 50. | CH₃ | CH₃ | CH₂CH₃ | 2 | 4-OCH₃ | 114. | H | OCH₃ | H | 3 | 4-OCH₃ |
| 51. | CH₃ | CH₃ | CH₂CH₃ | 3 | 4-OCH₃ | 115. | H | OCH₃ | H | 3 | 6-CH₃ |
| 52. | CH₃ | CH₃ | CH₂CH₃ | 3 | 6-CH₃ | 116. | H | OCH₃ | H | 2 | 4-CH₃ |
| 53. | CH₃ | CH₃ | CH₂CH₃ | 2 | 4-CH₃ | 117. | H | OCH₃ | H | 3 | 4-CH₃ |
| 54. | CH₃ | CH₃ | CH₂CH₃ | 3 | 4-CH₃ | 118. | CH₃ | OCH₃ | H | 2 | H |
| 55. | H | CH₃ | CH₂CH₂CH₃ | 2 | H | 119. | CH₃ | OCH₃ | H | 3 | H |
| 56. | H | CH₃ | CH₂CH₂CH₃ | 3 | H | 120. | CH₃ | OCH₃ | H | 4 | H |
| 57. | H | CH₃ | CH₂CH₂CH₃ | 4 | H | 121. | CH₃ | OCH₃ | H | 3 | 6-OCH₃ |
| 58. | H | CH₃ | CH₂CH₂CH₃ | 3 | 6-OCH₃ | 122. | CH₃ | OCH₃ | H | 2 | 4-OCH₃ |
| 59. | H | CH₃ | CH₂CH₂CH₃ | 2 | 4-OCH₃ | 123. | CH₃ | OCH₃ | H | 3 | 4-OCH₃ |
| 60. | H | CH₃ | CH₂CH₂CH₃ | 3 | 4-OCH₃ | 124. | CH₃ | OCH₃ | H | 3 | 6-CH₃ |
| 61. | H | CH₃ | CH₂CH₂CH₃ | 3 | 6-CH₃ | 125. | CH₃ | OCH₃ | H | 2 | 4-CH₃ |
| 62. | H | CH₃ | CH₂CH₂CH₃ | 2 | 4-CH₃ | 126. | CH₃ | OCH₃ | H | 3 | 4-CH₃ |
| 63. | H | CH₃ | CH₂CH₂CH₃ | 3 | 4-CH₃ | 127. | H | OCH₃ | CH₃ | 2 | H |
| 64. | CH₃ | CH₃ | CH₂CH₂CH₃ | 2 | H | 128. | H | OCH₃ | CH₃ | 3 | H |
| 65. | CH₃ | CH₃ | CH₂CH₂CH₃ | 3 | H | 129. | H | OCH₃ | CH₃ | 4 | H |
| 66. | CH₃ | CH₃ | CH₂CH₂CH₃ | 4 | H | 130. | H | OCH₃ | CH₃ | 3 | 6-OCH₃ |
| 67. | CH₃ | CH₃ | CH₂CH₂CH₃ | 3 | 6-OCH₃ | 131. | H | OCH₃ | CH₃ | 2 | 4-OCH₃ |
| 68. | CH₃ | CH₃ | CH₂CH₂CH₃ | 2 | 4-OCH₃ | 132. | H | OCH₃ | CH₃ | 3 | 4-OCH₃ |
| 69. | CH₃ | CH₃ | CH₂CH₂CH₃ | 3 | 4-OCH₃ | 133. | H | OCH₃ | CH₃ | 3 | 6-CH₃ |
| 70. | CH₃ | CH₃ | CH₂CH₂CH₃ | 3 | 6-CH₃ | 134. | H | OCH₃ | CH₃ | 2 | 4-CH₃ |
| 71. | CH₃ | CH₃ | CH₂CH₂CH₃ | 2 | 4-CH₃ | 135. | H | OCH₃ | CH₃ | 3 | 4-CH₃ |
| 72. | CH₃ | CH₃ | CH₂CH₂CH₃ | 3 | 4-CH₃ | 136. | CH₃ | OCH₃ | CH₃ | 2 | H |
| 73. | H | CH₃ | i-Pr | 2 | H | 137. | CH₃ | OCH₃ | CH₃ | 3 | H |
| 74. | H | CH₃ | i-Pr | 3 | H | 138. | CH₃ | OCH₃ | CH₃ | 4 | H |
| 75. | H | CH₃ | i-Pr | 4 | H | 139. | CH₃ | OCH₃ | CH₃ | 3 | 6-OCH₃ |
| 76. | H | CH₃ | i-Pr | 3 | 6-OCH₃ | 140. | CH₃ | OCH₃ | CH₃ | 2 | 4-OCH₃ |
| 77. | H | CH₃ | i-Pr | 2 | 4-OCH₃ | 141. | CH₃ | OCH₃ | CH₃ | 3 | 4-OCH₃ |
| 78. | H | CH₃ | i-Pr | 3 | 4-OCH₃ | 142. | CH₃ | OCH₃ | CH₃ | 3 | 6-CH₃ |
| 79. | H | CH₃ | i-Pr | 3 | 6-CH₃ | 143. | CH₃ | OCH₃ | CH₃ | 2 | 4-CH₃ |
| 80. | H | CH₃ | i-Pr | 2 | 4-CH₃ | 144. | CH₃ | OCH₃ | CH₃ | 3 | 4-CH₃ |
| 81. | H | CH₃ | i-Pr | 3 | 4-CH₃ | 145. | H | OCH₃ | CH₂CH₃ | 2 | H |
| 82. | CH₃ | CH₃ | i-Pr | 2 | H | 146. | H | OCH₃ | CH₂CH₃ | 3 | H |
| 83. | CH₃ | CH₃ | i-Pr | 3 | H | 147. | H | OCH₃ | CH₂CH₃ | 4 | H |
| 84. | CH₃ | CH₃ | i-Pr | 4 | H | 148. | H | OCH₃ | CH₂CH₃ | 3 | 6-OCH₃ |
| 85. | CH₃ | CH₃ | i-Pr | 3 | 6-OCH₃ | 149. | H | OCH₃ | CH₂CH₃ | 2 | 4-OCH₃ |
| 86. | CH₃ | CH₃ | i-Pr | 2 | 4-OCH₃ | 150. | H | OCH₃ | CH₂CH₃ | 3 | 4-OCH₃ |
| 87. | CH₃ | CH₃ | i-Pr | 3 | 4-OCH₃ | 151. | H | OCH₃ | CH₂CH₃ | 3 | 6-CH₃ |
| 88. | CH₃ | CH₃ | i-Pr | 3 | 6-CH₃ | 152. | H | OCH₃ | CH₂CH₃ | 2 | 4-CH₃ |
| 89. | CH₃ | CH₃ | i-Pr | 2 | 4-CH₃ | 153. | H | OCH₃ | CH₂CH₃ | 3 | 4-CH₃ |
| 90. | CH₃ | CH₃ | i-Pr | 3 | 4-CH₃ | 154. | CH₃ | OCH₃ | CH₂CH₃ | 2 | H |

TABLE A-continued (I-1)

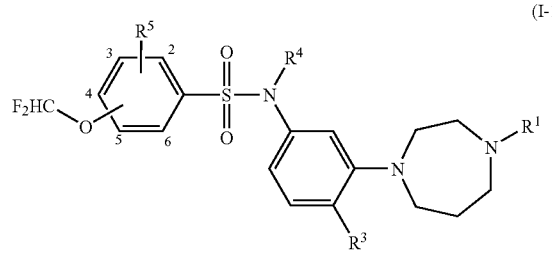

| No. | R¹ | R³ | R⁴ | position of OCHF₂ * | R⁵ * |
|---|---|---|---|---|---|
| 155. | CH₃ | OCH₃ | CH₂CH₃ | 3 | H |
| 156. | CH₃ | OCH₃ | CH₂CH₃ | 4 | H |
| 157. | CH₃ | OCH₃ | CH₂CH₃ | 3 | 6-OCH₃ |
| 158. | CH₃ | OCH₃ | CH₂CH₃ | 2 | 4-OCH₃ |
| 159. | CH₃ | OCH₃ | CH₂CH₃ | 3 | 4-OCH₃ |
| 160. | CH₃ | OCH₃ | CH₂CH₃ | 3 | 6-CH₃ |
| 161. | CH₃ | OCH₃ | CH₂CH₃ | 2 | 4-CH₃ |
| 162. | CH₃ | OCH₃ | CH₂CH₃ | 3 | 4-CH₃ |
| 163. | H | OCH₃ | CH₂CH₂CH₃ | 2 | H |
| 164. | H | OCH₃ | CH₂CH₂CH₃ | 3 | H |
| 165. | H | OCH₃ | CH₂CH₂CH₃ | 4 | H |
| 166. | H | OCH₃ | CH₂CH₂CH₃ | 3 | 6-OCH₃ |
| 167. | H | OCH₃ | CH₂CH₂CH₃ | 2 | 4-OCH₃ |
| 168. | H | OCH₃ | CH₂CH₂CH₃ | 3 | 4-OCH₃ |
| 169. | H | OCH₃ | CH₂CH₂CH₃ | 3 | 6-CH₃ |
| 170. | H | OCH₃ | CH₂CH₂CH₃ | 2 | 4-CH₃ |
| 171. | H | OCH₃ | CH₂CH₂CH₃ | 3 | 4-CH₃ |
| 172. | CH₃ | OCH₃ | CH₂CH₂CH₃ | 2 | H |
| 173. | CH₃ | OCH₃ | CH₂CH₂CH₃ | 3 | H |
| 174. | CH₃ | OCH₃ | CH₂CH₂CH₃ | 4 | H |
| 175. | CH₃ | OCH₃ | CH₂CH₂CH₃ | 3 | 6-OCH₃ |
| 176. | CH₃ | OCH₃ | CH₂CH₂CH₃ | 2 | 4-OCH₃ |
| 177. | CH₃ | OCH₃ | CH₂CH₂CH₃ | 3 | 4-OCH₃ |
| 178. | CH₃ | OCH₃ | CH₂CH₂CH₃ | 3 | 6-CH₃ |
| 179. | CH₃ | OCH₃ | CH₂CH₂CH₃ | 2 | 4-CH₃ |
| 180. | CH₃ | OCH₃ | CH₂CH₂CH₃ | 3 | 4-CH₃ |
| 181. | H | OCH₃ | i-Pr | 2 | H |
| 182. | H | OCH₃ | i-Pr | 3 | H |
| 183. | H | OCH₃ | i-Pr | 4 | H |
| 184. | H | OCH₃ | i-Pr | 3 | 6-OCH₃ |
| 185. | H | OCH₃ | i-Pr | 2 | 4-OCH₃ |
| 186. | H | OCH₃ | i-Pr | 3 | 4-OCH₃ |
| 187. | H | OCH₃ | i-Pr | 3 | 6-CH₃ |
| 188. | H | OCH₃ | i-Pr | 2 | 4-CH₃ |
| 189. | H | OCH₃ | i-Pr | 3 | 4-CH₃ |
| 190. | CH₃ | OCH₃ | i-Pr | 2 | H |
| 191. | CH₃ | OCH₃ | i-Pr | 3 | H |
| 192. | CH₃ | OCH₃ | i-Pr | 4 | H |
| 193. | CH₃ | OCH₃ | i-Pr | 3 | 6-OCH₃ |
| 194. | CH₃ | OCH₃ | i-Pr | 2 | 4-OCH₃ |
| 195. | CH₃ | OCH₃ | i-Pr | 3 | 4-OCH₃ |
| 196. | CH₃ | OCH₃ | i-Pr | 3 | 6-CH₃ |
| 197. | CH₃ | OCH₃ | i-Pr | 2 | 4-CH₃ |
| 198. | CH₃ | OCH₃ | i-Pr | 3 | 4-CH₃ |
| 199. | H | OCH₃ | CH₂—c-Pr | 2 | H |
| 200. | H | OCH₃ | CH₂—c-Pr | 3 | H |
| 201. | H | OCH₃ | CH₂—c-Pr | 4 | H |
| 202. | H | OCH₃ | CH₂—c-Pr | 3 | 6-OCH₃ |
| 203. | H | OCH₃ | CH₂—c-Pr | 2 | 4-OCH₃ |
| 204. | H | OCH₃ | CH₂—c-Pr | 3 | 4-OCH₃ |
| 205. | H | OCH₃ | CH₂—c-Pr | 3 | 6-CH₃ |
| 206. | H | OCH₃ | CH₂—c-Pr | 2 | 4-CH₃ |
| 207. | H | OCH₃ | CH₂—c-Pr | 3 | 4-CH₃ |
| 208. | CH₃ | OCH₃ | CH₂—c-Pr | 2 | H |
| 209. | CH₃ | OCH₃ | CH₂—c-Pr | 3 | H |
| 210. | CH₃ | OCH₃ | CH₂—c-Pr | 4 | H |
| 211. | CH₃ | OCH₃ | CH₂—c-Pr | 3 | 6-OCH₃ |
| 212. | CH₃ | OCH₃ | CH₂—c-Pr | 2 | 4-OCH₃ |
| 213. | CH₃ | OCH₃ | CH₂—c-Pr | 3 | 4-OCH₃ |
| 214. | CH₃ | OCH₃ | CH₂—c-Pr | 3 | 6-CH₃ |
| 215. | CH₃ | OCH₃ | CH₂—c-Pr | 2 | 4-CH₃ |
| 216. | CH₃ | OCH₃ | CH₂—c-Pr | 3 | 4-CH₃ |
| 217. | H | OCHF₂ | H | 2 | H |
| 218. | H | OCHF₂ | H | 3 | H |
| 219. | H | OCHF₂ | H | 4 | H |
| 220. | H | OCHF₂ | H | 3 | 6-OCH₃ |
| 221. | H | OCHF₂ | H | 2 | 4-OCH₃ |
| 222. | H | OCHF₂ | H | 3 | 4-OCH₃ |
| 223. | H | OCHF₂ | H | 3 | 6-CH₃ |
| 224. | H | OCHF₂ | H | 2 | 4-CH₃ |
| 225. | H | OCHF₂ | H | 3 | 4-CH₃ |
| 226. | CH₃ | OCHF₂ | H | 2 | H |
| 227. | CH₃ | OCHF₂ | H | 3 | H |
| 228. | CH₃ | OCHF₂ | H | 4 | H |
| 229. | CH₃ | OCHF₂ | H | 3 | 6-OCH₃ |
| 230. | CH₃ | OCHF₂ | H | 2 | 4-OCH₃ |
| 231. | CH₃ | OCHF₂ | H | 3 | 4-OCH₃ |
| 232. | CH₃ | OCHF₂ | H | 3 | 6-CH₃ |
| 233. | CH₃ | OCHF₂ | H | 2 | 4-CH₃ |
| 234. | CH₃ | OCHF₂ | H | 3 | 4-CH₃ |
| 235. | H | OCHF₂ | CH₃ | 2 | H |
| 236. | H | OCHF₂ | CH₃ | 3 | H |
| 237. | H | OCHF₂ | CH₃ | 4 | H |
| 238. | H | OCHF₂ | CH₃ | 3 | 6-OCH₃ |
| 239. | H | OCHF₂ | CH₃ | 2 | 4-OCH₃ |
| 240. | H | OCHF₂ | CH₃ | 3 | 4-OCH₃ |
| 241. | H | OCHF₂ | CH₃ | 3 | 6-CH₃ |
| 242. | H | OCHF₂ | CH₃ | 2 | 4-CH₃ |
| 243. | H | OCHF₂ | CH₃ | 3 | 4-CH₃ |
| 244. | CH₃ | OCHF₂ | CH₃ | 2 | H |
| 245. | CH₃ | OCHF₂ | CH₃ | 3 | H |
| 246. | CH₃ | OCHF₂ | CH₃ | 4 | H |
| 247. | CH₃ | OCHF₂ | CH₃ | 3 | 6-OCH₃ |
| 248. | CH₃ | OCHF₂ | CH₃ | 2 | 4-OCH₃ |
| 249. | CH₃ | OCHF₂ | CH₃ | 3 | 4-OCH₃ |
| 250. | CH₃ | OCHF₂ | CH₃ | 3 | 6-CH₃ |
| 251. | CH₃ | OCHF₂ | CH₃ | 2 | 4-CH₃ |
| 252. | CH₃ | OCHF₂ | CH₃ | 3 | 4-CH₃ |
| 253. | H | OCHF₂ | CH₂CH₃ | 2 | H |
| 254. | H | OCHF₂ | CH₂CH₃ | 3 | H |
| 255. | H | OCHF₂ | CH₂CH₃ | 4 | H |
| 256. | H | OCHF₂ | CH₂CH₃ | 3 | 6-OCH₃ |
| 257. | H | OCHF₂ | CH₂CH₃ | 2 | 4-OCH₃ |
| 258. | H | OCHF₂ | CH₂CH₃ | 3 | 4-OCH₃ |
| 259. | H | OCHF₂ | CH₂CH₃ | 3 | 6-CH₃ |
| 260. | H | OCHF₂ | CH₂CH₃ | 2 | 4-CH₃ |
| 261. | H | OCHF₂ | CH₂CH₃ | 3 | 4-CH₃ |
| 262. | CH₃ | OCHF₂ | CH₂CH₃ | 2 | H |
| 263. | CH₃ | OCHF₂ | CH₂CH₃ | 3 | H |
| 264. | CH₃ | OCHF₂ | CH₂CH₃ | 4 | H |
| 265. | CH₃ | OCHF₂ | CH₂CH₃ | 3 | 6-OCH₃ |
| 266. | CH₃ | OCHF₂ | CH₂CH₃ | 2 | 4-OCH₃ |
| 267. | CH₃ | OCHF₂ | CH₂CH₃ | 3 | 4-OCH₃ |
| 268. | CH₃ | OCHF₂ | CH₂CH₃ | 3 | 6-CH₃ |
| 269. | CH₃ | OCHF₂ | CH₂CH₃ | 2 | 4-CH₃ |
| 270. | CH₃ | OCHF₂ | CH₂CH₃ | 3 | 4-CH₃ |
| 271. | H | OCHF₂ | CH₂CH₂CH₃ | 2 | H |
| 272. | H | OCHF₂ | CH₂CH₂CH₃ | 3 | H |
| 273. | H | OCHF₂ | CH₂CH₂CH₃ | 4 | H |
| 274. | H | OCHF₂ | CH₂CH₂CH₃ | 3 | 6-OCH₃ |
| 275. | H | OCHF₂ | CH₂CH₂CH₃ | 2 | 4-OCH₃ |
| 276. | H | OCHF₂ | CH₂CH₂CH₃ | 3 | 4-OCH₃ |
| 277. | H | OCHF₂ | CH₂CH₂CH₃ | 3 | 6-CH₃ |
| 278. | H | OCHF₂ | CH₂CH₂CH₃ | 2 | 4-CH₃ |
| 279. | H | OCHF₂ | CH₂CH₂CH₃ | 3 | 4-CH₃ |
| 280. | CH₃ | OCHF₂ | CH₂CH₂CH₃ | 2 | H |
| 281. | CH₃ | OCHF₂ | CH₂CH₂CH₃ | 3 | H |
| 282. | CH₃ | OCHF₂ | CH₂CH₂CH₃ | 4 | H |

TABLE A-continued (I-1)

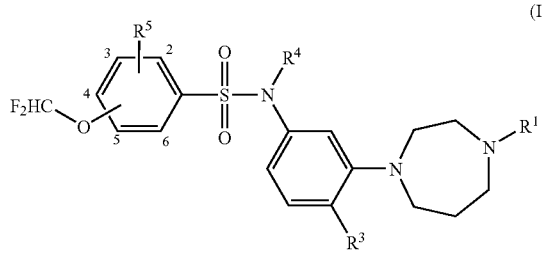

| No. | R¹ | R³ | R⁴ | position of OCHF₂ * | R⁵ * |
|---|---|---|---|---|---|
| 283. | CH₃ | OCHF₂ | CH₂CH₂CH₃ | 3 | 6-OCH₃ |
| 284. | CH₃ | OCHF₂ | CH₂CH₂CH₃ | 2 | 4-OCH₃ |
| 285. | CH₃ | OCHF₂ | CH₂CH₂CH₃ | 3 | 4-OCH₃ |
| 286. | CH₃ | OCHF₂ | CH₂CH₂CH₃ | 3 | 6-CH₃ |
| 287. | CH₃ | OCHF₂ | CH₂CH₂CH₃ | 2 | 4-CH₃ |
| 288. | CH₃ | OCHF₂ | CH₂CH₂CH₃ | 3 | 4-CH₃ |
| 289. | H | OCHF₂ | i-Pr | 2 | H |
| 290. | H | OCHF₂ | i-Pr | 3 | H |
| 291. | H | OCHF₂ | i-Pr | 4 | H |
| 292. | H | OCHF₂ | i-Pr | 3 | 6-OCH₃ |
| 293. | H | OCHF₂ | i-Pr | 2 | 4-OCH₃ |
| 294. | H | OCHF₂ | i-Pr | 3 | 4-OCH₃ |
| 295. | H | OCHF₂ | i-Pr | 3 | 6-CH₃ |
| 296. | H | OCHF₂ | i-Pr | 2 | 4-CH₃ |
| 297. | H | OCHF₂ | i-Pr | 3 | 4-CH₃ |
| 298. | CH₃ | OCHF₂ | i-Pr | 2 | H |
| 299. | CH₃ | OCHF₂ | i-Pr | 3 | H |
| 300. | CH₃ | OCHF₂ | i-Pr | 4 | H |
| 301. | CH₃ | OCHF₂ | i-Pr | 3 | 6-OCH₃ |
| 302. | CH₃ | OCHF₂ | i-Pr | 2 | 4-OCH₃ |
| 303. | CH₃ | OCHF₂ | i-Pr | 3 | 4-OCH₃ |
| 304. | CH₃ | OCHF₂ | i-Pr | 3 | 6-CH₃ |
| 305. | CH₃ | OCHF₂ | i-Pr | 2 | 4-CH₃ |
| 306. | CH₃ | OCHF₂ | i-Pr | 3 | 4-CH₃ |
| 307. | H | OCHF₂ | CH₂—c-Pr | 2 | H |
| 308. | H | OCHF₂ | CH₂—c-Pr | 3 | H |
| 309. | H | OCHF₂ | CH₂—c-Pr | 4 | H |
| 310. | H | OCHF₂ | CH₂—c-Pr | 3 | 6-OCH₃ |
| 311. | H | OCHF₂ | CH₂—c-Pr | 2 | 4-OCH₃ |
| 312. | H | OCHF₂ | CH₂—c-Pr | 3 | 4-OCH₃ |
| 313. | H | OCHF₂ | CH₂—c-Pr | 3 | 6-CH₃ |
| 314. | H | OCHF₂ | CH₂—c-Pr | 2 | 4-CH₃ |
| 315. | H | OCHF₂ | CH₂—c-Pr | 3 | 4-CH₃ |
| 316. | CH₃ | OCHF₂ | CH₂—c-Pr | 2 | H |
| 317. | CH₃ | OCHF₂ | CH₂—c-Pr | 3 | H |
| 318. | CH₃ | OCHF₂ | CH₂—c-Pr | 4 | H |
| 319. | CH₃ | OCHF₂ | CH₂—c-Pr | 3 | 6-OCH₃ |
| 320. | CH₃ | OCHF₂ | CH₂—c-Pr | 2 | 4-OCH₃ |
| 321. | CH₃ | OCHF₂ | CH₂—c-Pr | 3 | 4-OCH₃ |
| 322. | CH₃ | OCHF₂ | CH₂—c-Pr | 3 | 6-CH₃ |
| 323. | CH₃ | OCHF₂ | CH₂—c-Pr | 2 | 4-CH₃ |
| 324. | CH₃ | OCHF₂ | CH₂—c-Pr | 3 | 4-CH₃ |
| 325. | H | F | H | 2 | H |
| 326. | H | F | H | 3 | H |
| 327. | H | F | H | 4 | H |
| 328. | H | F | H | 3 | 6-OCH₃ |
| 329. | H | F | H | 2 | 4-OCH₃ |
| 330. | H | F | H | 3 | 4-OCH₃ |
| 331. | H | F | H | 3 | 6-CH₃ |
| 332. | H | F | H | 2 | 4-CH₃ |
| 333. | H | F | H | 3 | 4-CH₃ |
| 334. | CH₃ | F | H | 2 | H |
| 335. | CH₃ | F | H | 3 | H |
| 336. | CH₃ | F | H | 4 | H |
| 337. | CH₃ | F | H | 3 | 6-OCH₃ |
| 338. | CH₃ | F | H | 2 | 4-OCH₃ |
| 339. | CH₃ | F | H | 3 | 4-OCH₃ |
| 340. | CH₃ | F | H | 3 | 6-CH₃ |
| 341. | CH₃ | F | H | 2 | 4-CH₃ |
| 342. | CH₃ | F | H | 3 | 4-CH₃ |
| 343. | H | F | CH₃ | 2 | H |
| 344. | H | F | CH₃ | 3 | H |
| 345. | H | F | CH₃ | 4 | H |
| 346. | H | F | CH₃ | 3 | 6-OCH₃ |
| 347. | H | F | CH₃ | 2 | 4-OCH₃ |
| 348. | H | F | CH₃ | 3 | 4-OCH₃ |
| 349. | H | F | CH₃ | 3 | 6-CH₃ |
| 350. | H | F | CH₃ | 2 | 4-CH₃ |
| 351. | H | F | CH₃ | 3 | 4-CH₃ |
| 352. | CH₃ | F | CH₃ | 2 | H |
| 353. | CH₃ | F | CH₃ | 3 | H |
| 354. | CH₃ | F | CH₃ | 4 | H |
| 355. | CH₃ | F | CH₃ | 3 | 6-OCH₃ |
| 356. | CH₃ | F | CH₃ | 2 | 4-OCH₃ |
| 357. | CH₃ | F | CH₃ | 3 | 4-OCH₃ |
| 358. | CH₃ | F | CH₃ | 3 | 6-CH₃ |
| 359. | CH₃ | F | CH₃ | 2 | 4-CH₃ |
| 360. | CH₃ | F | CH₃ | 3 | 4-CH₃ |
| 361. | H | F | CH₂CH₃ | 2 | H |
| 362. | H | F | CH₂CH₃ | 3 | H |
| 363. | H | F | CH₂CH₃ | 4 | H |
| 364. | H | F | CH₂CH₃ | 3 | 6-OCH₃ |
| 365. | H | F | CH₂CH₃ | 2 | 4-OCH₃ |
| 366. | H | F | CH₂CH₃ | 3 | 4-OCH₃ |
| 367. | H | F | CH₂CH₃ | 3 | 6-CH₃ |
| 368. | H | F | CH₂CH₃ | 2 | 4-CH₃ |
| 369. | H | F | CH₂CH₃ | 3 | 4-CH₃ |
| 370. | CH₃ | F | CH₂CH₃ | 2 | H |
| 371. | CH₃ | F | CH₂CH₃ | 3 | H |
| 372. | CH₃ | F | CH₂CH₃ | 4 | H |
| 373. | CH₃ | F | CH₂CH₃ | 3 | 6-OCH₃ |
| 374. | CH₃ | F | CH₂CH₃ | 2 | 4-OCH₃ |
| 375. | CH₃ | F | CH₂CH₃ | 3 | 4-OCH₃ |
| 376. | CH₃ | F | CH₂CH₃ | 3 | 6-CH₃ |
| 377. | CH₃ | F | CH₂CH₃ | 2 | 4-CH₃ |
| 378. | CH₃ | F | CH₂CH₃ | 3 | 4-CH₃ |
| 379. | H | F | CH₂CH₂CH₃ | 2 | H |
| 380. | H | F | CH₂CH₂CH₃ | 3 | H |
| 381. | H | F | CH₂CH₂CH₃ | 4 | H |
| 382. | H | F | CH₂CH₂CH₃ | 3 | 6-OCH₃ |
| 383. | H | F | CH₂CH₂CH₃ | 2 | 4-OCH₃ |
| 384. | H | F | CH₂CH₂CH₃ | 3 | 4-OCH₃ |
| 385. | H | F | CH₂CH₂CH₃ | 3 | 6-CH₃ |
| 386. | H | F | CH₂CH₂CH₃ | 2 | 4-CH₃ |
| 387. | H | F | CH₂CH₂CH₃ | 3 | 4-CH₃ |
| 388. | CH₃ | F | CH₂CH₂CH₃ | 2 | H |
| 389. | CH₃ | F | CH₂CH₂CH₃ | 3 | H |
| 390. | CH₃ | F | CH₂CH₂CH₃ | 4 | H |
| 391. | CH₃ | F | CH₂CH₂CH₃ | 3 | 6-OCH₃ |
| 392. | CH₃ | F | CH₂CH₂CH₃ | 2 | 4-OCH₃ |
| 393. | CH₃ | F | CH₂CH₂CH₃ | 3 | 4-OCH₃ |
| 394. | CH₃ | F | CH₂CH₂CH₃ | 3 | 6-CH₃ |
| 395. | CH₃ | F | CH₂CH₂CH₃ | 2 | 4-CH₃ |
| 396. | CH₃ | F | CH₂CH₂CH₃ | 3 | 4-CH₃ |
| 397. | H | F | i-Pr | 2 | H |
| 398. | H | F | i-Pr | 3 | H |
| 399. | H | F | i-Pr | 4 | H |
| 400. | H | F | i-Pr | 3 | 6-OCH₃ |
| 401. | H | F | i-Pr | 2 | 4-OCH₃ |
| 402. | H | F | i-Pr | 3 | 4-OCH₃ |
| 403. | H | F | i-Pr | 3 | 6-CH₃ |
| 404. | H | F | i-Pr | 2 | 4-CH₃ |
| 405. | H | F | i-Pr | 3 | 4-CH₃ |
| 406. | CH₃ | F | i-Pr | 2 | H |
| 407. | CH₃ | F | i-Pr | 3 | H |
| 408. | CH₃ | F | i-Pr | 4 | H |
| 409. | CH₃ | F | i-Pr | 3 | 6-OCH₃ |
| 410. | CH₃ | F | i-Pr | 2 | 4-OCH₃ |

TABLE A-continued

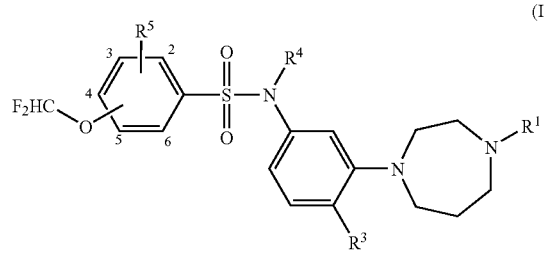

(I-1)

| No. | R¹ | R³ | R⁴ | position of OCHF₂ * | R⁵ * |
|---|---|---|---|---|---|
| 411. | CH₃ | F | i-Pr | 3 | 4-OCH₃ |
| 412. | CH₃ | F | i-Pr | 3 | 6-CH₃ |
| 413. | CH₃ | F | i-Pr | 2 | 4-CH₃ |
| 414. | CH₃ | F | i-Pr | 3 | 4-CH₃ |
| 415. | H | F | CH₂—c-Pr | 2 | H |
| 416. | H | F | CH₂—c-Pr | 3 | H |
| 417. | H | F | CH₂—c-Pr | 4 | H |
| 418. | H | F | CH₂—c-Pr | 3 | 6-OCH₃ |
| 419. | H | F | CH₂—c-Pr | 2 | 4-OCH₃ |
| 420. | H | F | CH₂—c-Pr | 3 | 4-OCH₃ |
| 421. | H | F | CH₂—c-Pr | 3 | 6-CH₃ |
| 422. | H | F | CH₂—c-Pr | 2 | 4-CH₃ |
| 423. | H | F | CH₂—c-Pr | 3 | 4-CH₃ |
| 424. | CH₃ | F | CH₂—c-Pr | 2 | H |
| 425. | CH₃ | F | CH₂—c-Pr | 3 | H |
| 426. | CH₃ | F | CH₂—c-Pr | 4 | H |
| 427. | CH₃ | F | CH₂—c-Pr | 3 | 6-OCH₃ |
| 428. | CH₃ | F | CH₂—c-Pr | 2 | 4-OCH₃ |
| 429. | CH₃ | F | CH₂—c-Pr | 3 | 4-OCH₃ |
| 430. | CH₃ | F | CH₂—c-Pr | 3 | 6-CH₃ |
| 431. | CH₃ | F | CH₂—c-Pr | 2 | 4-CH₃ |
| 432. | CH₃ | F | CH₂—c-Pr | 3 | 4-CH₃ |
| 433. | H | H | H | 2 | H |
| 434. | H | H | H | 3 | H |
| 435. | H | H | H | 4 | H |
| 436. | H | H | H | 3 | 6-OCH₃ |
| 437. | H | H | H | 2 | 4-OCH₃ |
| 438. | H | H | H | 3 | 4-OCH₃ |
| 439. | H | H | H | 3 | 6-CH₃ |
| 440. | H | H | H | 2 | 4-CH₃ |
| 441. | H | H | H | 3 | 4-CH₃ |
| 442. | CH₃ | H | H | 2 | H |
| 443. | CH₃ | H | H | 3 | H |
| 444. | CH₃ | H | H | 4 | H |
| 445. | CH₃ | H | H | 3 | 6-OCH₃ |
| 446. | CH₃ | H | H | 2 | 4-OCH₃ |
| 447. | CH₃ | H | H | 3 | 4-OCH₃ |
| 448. | CH₃ | H | H | 3 | 6-CH₃ |
| 449. | CH₃ | H | H | 2 | 4-CH₃ |
| 450. | CH₃ | H | H | 3 | 4-CH₃ |
| 451. | H | H | CH₃ | 2 | H |
| 452. | H | H | CH₃ | 3 | H |
| 453. | H | H | CH₃ | 4 | H |
| 454. | H | H | CH₃ | 3 | 6-OCH₃ |
| 455. | H | H | CH₃ | 2 | 4-OCH₃ |
| 456. | H | H | CH₃ | 3 | 4-OCH₃ |
| 457. | H | H | CH₃ | 3 | 6-CH₃ |
| 458. | H | H | CH₃ | 2 | 4-CH₃ |
| 459. | H | H | CH₃ | 3 | 4-CH₃ |
| 460. | CH₃ | H | CH₃ | 2 | H |
| 461. | CH₃ | H | CH₃ | 3 | H |
| 462. | CH₃ | H | CH₃ | 4 | H |
| 463. | CH₃ | H | CH₃ | 3 | 6-OCH₃ |
| 464. | CH₃ | H | CH₃ | 2 | 4-OCH₃ |
| 465. | CH₃ | H | CH₃ | 3 | 4-OCH₃ |
| 466. | CH₃ | H | CH₃ | 3 | 6-CH₃ |
| 467. | CH₃ | H | CH₃ | 2 | 4-CH₃ |
| 468. | CH₃ | H | CH₃ | 3 | 4-CH₃ |
| 469. | H | H | CH₂CH₃ | 2 | H |
| 470. | H | H | CH₂CH₃ | 3 | H |
| 471. | H | H | CH₂CH₃ | 4 | H |
| 472. | H | H | CH₂CH₃ | 3 | 6-OCH₃ |
| 473. | H | H | CH₂CH₃ | 2 | 4-OCH₃ |
| 474. | H | H | CH₂CH₃ | 3 | 4-OCH₃ |
| 475. | H | H | CH₂CH₃ | 3 | 6-CH₃ |
| 476. | H | H | CH₂CH₃ | 2 | 4-CH₃ |
| 477. | H | H | CH₂CH₃ | 3 | 4-CH₃ |
| 478. | CH₃ | H | CH₂CH₃ | 2 | H |
| 479. | CH₃ | H | CH₂CH₃ | 3 | H |
| 480. | CH₃ | H | CH₂CH₃ | 4 | H |
| 481. | CH₃ | H | CH₂CH₃ | 3 | 6-OCH₃ |
| 482. | CH₃ | H | CH₂CH₃ | 2 | 4-OCH₃ |
| 483. | CH₃ | H | CH₂CH₃ | 3 | 4-OCH₃ |
| 484. | CH₃ | H | CH₂CH₃ | 3 | 6-CH₃ |
| 485. | CH₃ | H | CH₂CH₃ | 2 | 4-CH₃ |
| 486. | CH₃ | H | CH₂CH₃ | 3 | 4-CH₃ |
| 487. | H | H | CH₂CH₂CH₃ | 2 | H |
| 488. | H | H | CH₂CH₂CH₃ | 3 | H |
| 489. | H | H | CH₂CH₂CH₃ | 4 | H |
| 490. | H | H | CH₂CH₂CH₃ | 3 | 6-OCH₃ |
| 491. | H | H | CH₂CH₂CH₃ | 2 | 4-OCH₃ |
| 492. | H | H | CH₂CH₂CH₃ | 3 | 4-OCH₃ |
| 493. | H | H | CH₂CH₂CH₃ | 3 | 6-CH₃ |
| 494. | H | H | CH₂CH₂CH₃ | 2 | 4-CH₃ |
| 495. | H | H | CH₂CH₂CH₃ | 3 | 4-CH₃ |
| 496. | CH₃ | H | CH₂CH₂CH₃ | 2 | H |
| 497. | CH₃ | H | CH₂CH₂CH₃ | 3 | H |
| 498. | CH₃ | H | CH₂CH₂CH₃ | 4 | H |
| 499. | CH₃ | H | CH₂CH₂CH₃ | 3 | 6-OCH₃ |
| 500. | CH₃ | H | CH₂CH₂CH₃ | 2 | 4-OCH₃ |
| 501. | CH₃ | H | CH₂CH₂CH₃ | 3 | 4-OCH₃ |
| 502. | CH₃ | H | CH₂CH₂CH₃ | 3 | 6-CH₃ |
| 503. | CH₃ | H | CH₂CH₂CH₃ | 2 | 4-CH₃ |
| 504. | CH₃ | H | CH₂CH₂CH₃ | 3 | 4-CH₃ |
| 505. | H | H | i-Pr | 2 | H |
| 506. | H | H | i-Pr | 3 | H |
| 507. | H | H | i-Pr | 4 | H |
| 508. | H | H | i-Pr | 3 | 6-OCH₃ |
| 509. | H | H | i-Pr | 2 | 4-OCH₃ |
| 510. | H | H | i-Pr | 3 | 4-OCH₃ |
| 511. | H | H | i-Pr | 3 | 6-CH₃ |
| 512. | H | H | i-Pr | 2 | 4-CH₃ |
| 513. | H | H | i-Pr | 3 | 4-CH₃ |
| 514. | CH₃ | H | i-Pr | 2 | H |
| 515. | CH₃ | H | i-Pr | 3 | H |
| 516. | CH₃ | H | i-Pr | 4 | H |
| 517. | CH₃ | H | i-Pr | 3 | 6-OCH₃ |
| 518. | CH₃ | H | i-Pr | 2 | 4-OCH₃ |
| 519. | CH₃ | H | i-Pr | 3 | 4-OCH₃ |
| 520. | CH₃ | H | i-Pr | 3 | 6-CH₃ |
| 521. | CH₃ | H | i-Pr | 2 | 4-CH₃ |
| 522. | CH₃ | H | i-Pr | 3 | 4-CH₃ |
| 523. | H | H | CH₂—c-Pr | 2 | H |
| 524. | H | H | CH₂—c-Pr | 3 | H |
| 525. | H | H | CH₂—c-Pr | 4 | H |
| 526. | H | H | CH₂—c-Pr | 3 | 6-OCH₃ |
| 527. | H | H | CH₂—c-Pr | 2 | 4-OCH₃ |
| 528. | H | H | CH₂—c-Pr | 3 | 4-OCH₃ |
| 529. | H | H | CH₂—c-Pr | 3 | 6-CH₃ |
| 530. | H | H | CH₂—c-Pr | 2 | 4-CH₃ |
| 531. | H | H | CH₂—c-Pr | 3 | 4-CH₃ |
| 532. | CH₃ | H | CH₂—c-Pr | 2 | H |
| 533. | CH₃ | H | CH₂—c-Pr | 3 | H |
| 534. | CH₃ | H | CH₂—c-Pr | 4 | H |
| 535. | CH₃ | H | CH₂—c-Pr | 3 | 6-OCH₃ |
| 536. | CH₃ | H | CH₂—c-Pr | 2 | 4-OCH₃ |
| 537. | CH₃ | H | CH₂—c-Pr | 3 | 4-OCH₃ |
| 538. | CH₃ | H | CH₂—c-Pr | 3 | 6-CH₃ |

TABLE A-continued

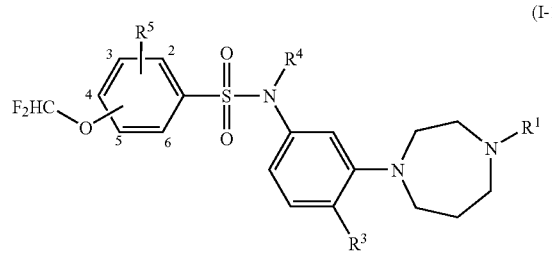

(I-1)

| No. | R¹ | R³ | R⁴ | position of OCHF₂ * | R⁵ * |
|---|---|---|---|---|---|
| 539. | CH₃ | H | CH₂—c-Pr | 2 | 4-CH₃ |
| 540. | CH₃ | H | CH₂—c-Pr | 3 | 4-CH₃ |

* position with respect to the sulfonyl moiety (ortho = 2-position, meta = 3-position, para = 4-position);
CH₂—c-Pr = cyclopropylmethyl;
i-Pr = isopropyl.

Preferred compounds according to the present invention are the compounds of the formula I', their pharmacologically tolerated salts and the N-oxides thereof, wherein $R^2$, $R^5$ and $R^6$ are hydrogen and wherein $R^1$, $R^3$, $R^4$ and the position of the sulfonyl group on the benzene ring with respect to the dioxole ring are as defined above. These compounds are hereinafter referred to as compounds of the formula I'-1. Examples are given in the following table B:

TABLE B

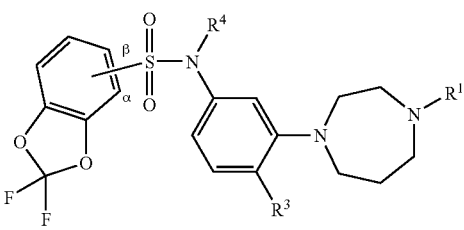

(I'-1)

| No. | R¹ | R³ | R⁴ | Position of SO₂ * |
|---|---|---|---|---|
| 541. | H | CH₃ | H | α |
| 542. | H | CH₃ | H | β |
| 543. | H | CH₃ | CH₃ | α |
| 544. | H | CH₃ | CH₃ | β |
| 545. | H | CH₃ | CH₂CH₃ | α |
| 546. | H | CH₃ | CH₂CH₃ | β |
| 547. | H | CH₃ | CH₂CH₂CH₃ | α |
| 548. | H | CH₃ | CH₂CH₂CH₃ | β |
| 549. | H | CH₃ | i-Pr | α |
| 550. | H | CH₃ | i-Pr | β |
| 551. | H | CH₃ | CH₂—c-Pr | α |
| 552. | H | CH₃ | CH₂—c-Pr | β |
| 553. | CH₃ | CH₃ | H | α |
| 554. | CH₃ | CH₃ | H | β |
| 555. | CH₃ | CH₃ | CH₃ | α |
| 556. | CH₃ | CH₃ | CH₃ | β |
| 557. | CH₃ | CH₃ | CH₂CH₃ | α |
| 558. | CH₃ | CH₃ | CH₂CH₃ | β |
| 559. | CH₃ | CH₃ | CH₂CH₂CH₃ | α |
| 560. | CH₃ | CH₃ | CH₂CH₂CH₃ | β |
| 561. | CH₃ | CH₃ | i-Pr | α |
| 562. | CH₃ | CH₃ | i-Pr | β |
| 563. | CH₃ | CH₃ | CH₂—c-Pr | α |
| 564. | CH₃ | CH₃ | CH₂—c-Pr | β |
| 565. | H | OCH₃ | H | α |
| 566. | H | OCH₃ | H | β |
| 567. | H | OCH₃ | CH₃ | α |
| 568. | H | OCH₃ | CH₃ | β |
| 569. | H | OCH₃ | CH₂CH₃ | α |
| 570. | H | OCH₃ | CH₂CH₃ | β |
| 571. | H | OCH₃ | CH₂CH₂CH₃ | α |
| 572. | H | OCH₃ | CH₂CH₂CH₃ | β |
| 573. | H | OCH₃ | i-Pr | α |
| 574. | H | OCH₃ | i-Pr | β |
| 575. | H | OCH₃ | CH₂—c-Pr | α |
| 576. | H | OCH₃ | CH₂—c-Pr | β |
| 577. | CH₃ | OCH₃ | H | α |
| 578. | CH₃ | OCH₃ | H | β |
| 579. | CH₃ | OCH₃ | CH₃ | α |
| 580. | CH₃ | OCH₃ | CH₃ | β |
| 581. | CH₃ | OCH₃ | CH₂CH₃ | α |
| 582. | CH₃ | OCH₃ | CH₂CH₃ | β |
| 583. | CH₃ | OCH₃ | CH₂CH₂CH₃ | α |
| 584. | CH₃ | OCH₃ | CH₂CH₂CH₃ | β |
| 585. | CH₃ | OCH₃ | i-Pr | α |
| 586. | CH₃ | OCH₃ | i-Pr | β |
| 587. | CH₃ | OCH₃ | CH₂—c-Pr | α |
| 588. | CH₃ | OCH₃ | CH₂—c-Pr | β |
| 589. | H | OCHF₂ | H | α |
| 590. | H | OCHF₂ | H | β |
| 591. | H | OCHF₂ | CH₃ | α |
| 592. | H | OCHF₂ | CH₃ | β |
| 593. | H | OCHF₂ | CH₂CH₃ | α |
| 594. | H | OCHF₂ | CH₂CH₃ | β |
| 595. | H | OCHF₂ | CH₂CH₂CH₃ | α |
| 596. | H | OCHF₂ | CH₂CH₂CH₃ | β |
| 597. | H | OCHF₂ | i-Pr | α |
| 598. | H | OCHF₂ | i-Pr | β |
| 599. | H | OCHF₂ | CH₂—c-Pr | α |
| 600. | H | OCHF₂ | CH₂—c-Pr | β |
| 601. | CH₃ | OCHF₂ | H | α |
| 602. | CH₃ | OCHF₂ | H | β |
| 603. | CH₃ | OCHF₂ | CH₃ | α |
| 604. | CH₃ | OCHF₂ | CH₃ | β |
| 605. | CH₃ | OCHF₂ | CH₂CH₃ | α |
| 606. | CH₃ | OCHF₂ | CH₂CH₃ | β |
| 607. | CH₃ | OCHF₂ | CH₂CH₂CH₃ | α |
| 608. | CH₃ | OCHF₂ | CH₂CH₂CH₃ | β |
| 609. | CH₃ | OCHF₂ | i-Pr | α |
| 610. | CH₃ | OCHF₂ | i-Pr | β |
| 611. | CH₃ | OCHF₂ | CH₂—c-Pr | α |
| 612. | CH₃ | OCHF₂ | CH₂—c-Pr | β |
| 613. | H | F | H | α |
| 614. | H | F | H | β |
| 615. | H | F | CH₃ | α |
| 616. | H | F | CH₃ | β |
| 617. | H | F | CH₂CH₃ | α |
| 618. | H | F | CH₂CH₃ | β |
| 619. | H | F | CH₂CH₂CH₃ | α |
| 620. | H | F | CH₂CH₂CH₃ | β |
| 621. | H | F | i-Pr | α |
| 622. | H | F | i-Pr | β |
| 623. | H | F | CH₂—c-Pr | α |
| 624. | H | F | CH₂—c-Pr | β |
| 625. | CH₃ | F | H | α |
| 626. | CH₃ | F | H | β |
| 627. | CH₃ | F | CH₃ | α |
| 628. | CH₃ | F | CH₃ | β |
| 629. | CH₃ | F | CH₂CH₃ | α |
| 630. | CH₃ | F | CH₂CH₃ | β |
| 631. | CH₃ | F | CH₂CH₂CH₃ | α |

TABLE B-continued (I'-1)

| | $R^1$ | $R^3$ | $R^4$ | Position of $SO_2$* |
|---|---|---|---|---|
| 632. | $CH_3$ | F | $CH_2CH_2CH_3$ | β |
| 633. | $CH_3$ | F | i-Pr | α |
| 634. | $CH_3$ | F | i-Pr | β |
| 635. | $CH_3$ | F | $CH_2$—c-Pr | α |
| 636. | $CH_3$ | F | $CH_2$—c-Pr | β |
| 637. | H | H | H | α |
| 638. | H | H | H | β |
| 639. | H | H | $CH_3$ | α |
| 640. | H | H | $CH_3$ | β |
| 641. | H | H | $CH_2CH_3$ | α |
| 642. | H | H | $CH_2CH_3$ | β |
| 643. | H | H | $CH_2CH_2CH_3$ | α |
| 644. | H | H | $CH_2CH_2CH_3$ | β |
| 645. | H | H | i-Pr | α |
| 646. | H | H | i-Pr | β |
| 647. | H | H | $CH_2$—c-Pr | α |
| 648. | H | H | $CH_2$—c-Pr | β |
| 649. | $CH_3$ | H | H | α |
| 650. | $CH_3$ | H | H | β |
| 651. | $CH_3$ | H | $CH_3$ | α |
| 652. | $CH_3$ | H | $CH_3$ | β |
| 653. | $CH_3$ | H | $CH_2CH_3$ | α |
| 654. | $CH_3$ | H | $CH_2CH_3$ | β |
| 655. | $CH_3$ | H | $CH_2CH_2CH_3$ | α |
| 656. | $CH_3$ | H | $CH_2CH_2CH_3$ | β |
| 657. | $CH_3$ | H | i-Pr | α |
| 658. | $CH_3$ | H | i-Pr | β |
| 659. | $CH_3$ | H | $CH_2$—c-Pr | α |
| 660. | $CH_3$ | H | $CH_2$—c-Pr | β |

* position with respect to the dioxole ring;
$CH_2$—c-Pr = cyclopropylmethyl;
i-Pr = isopropyl.

The compounds I and I' according to the invention are prepared in analogy with methods known from the literature. An important approach to the compounds according to the invention is offered by the reaction of a 1-(homopiperazin-1-yl)-3-aminobenzene compound II with a difluoromethoxy benzenesulfonic acid derivative III as depicted in scheme 1 or with a 2,2-difluorobenzo[1,3]dioxolesulfonic acid derivative IIIa as depicted in scheme 1a.

Scheme 1:

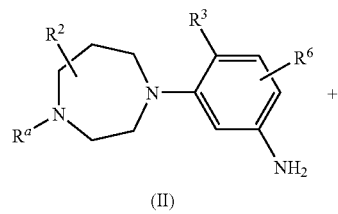

(II)

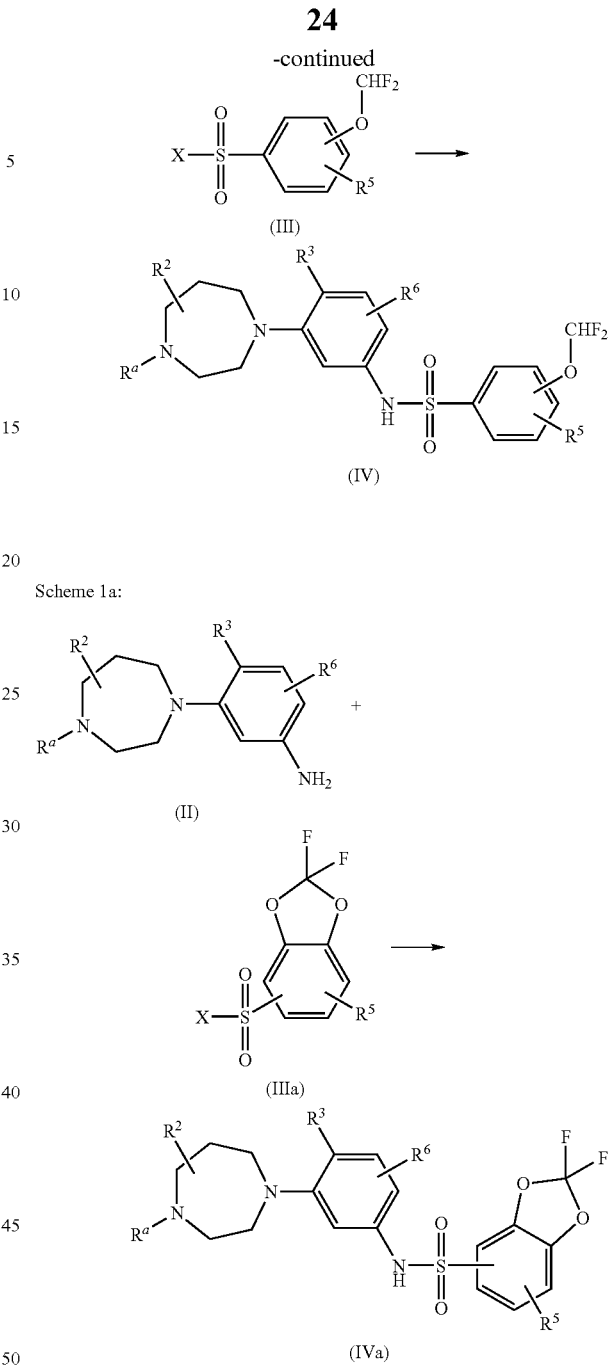

In schemes 1 and 1a, $R^2$, $R^3$, $R^5$ and $R^6$ have the previously mentioned meanings and $R^2$ is positioned vicinal to $R^a$. $R^a$ is a nitrogen protecting group or methyl. Suitable N-protecting groups are described, for example, in P. J. Kocienski "Protecting Groups", $2^{nd}$ ed., Georg Thieme Verlag, Stuttgart 2000, pp 186-237 and in the literature cited therein. Preferred examples of N-protecting groups are e.g. oxycarbonyl groups such as $C_1$-$C_6$-alkoxycarbonyl, e.g. methoxycarbonyl, ethoxycarbonyl and Boc (tert-butoxycarbonyl) and other oxycarbonyl groups such as benzyloxycarbonyl (Cbz), allyloxycarbonyl, 9-fluorenylmethoxycarbonyl (Fmoc) and 2-trimethylsilylethoxycarbonyl (Teoc), or 2-propenyl (allyl). X is a nucleophilically displaceable leaving group, in particular a halogen atom and, especially, chlorine or bromine.

Compounds of the formulae IV and IVa, wherein $R^a$ is a nitrogen protecting group, in particular a $C_1$-$C_6$-alkoxycarbonyl group such as methoxycarbonyl, ethoxycarbonyl and Boc (tert-butoxycarbonyl), are novel and thus form also part of the present invention. Compounds of the formula IV, wherein $R^a$ is methyl correspond to compounds I, wherein $R^1$ is methyl. Compounds of the formula IVa, wherein $R^a$ is methyl correspond to compounds I', wherein $R^1$ is methyl.

The reaction depicted in schemes 1 and 1a takes place under the reaction conditions which are customary for preparing arylsulfonamide compounds or arylsulfonic esters, respectively, and which are described, for example, in J. March, Advanced Organic Chemistry, $3^{rd}$ edition, John Wiley & Sons, New York, 1985, p. 444 and the literature cited therein; European J. Org. Chem. 2002 (13), pp. 2094-2108; Tetrahedron 2001, 57 (27), pp. 5885-5895; Bioorganic and Medicinal Chemistry Letters 2000, 10(8), pp. 835-838; and Synthesis 2000 (1), pp. 103-108.

The reaction customarily takes place in an inert solvent, for example in an ether, such as diethyl ether, diisopropyl ether, methyl tert-butyl ether or tetrahydrofuran, a halohydrocarbon, such as dichloromethane, an aliphatic or cycloaliphatic hydrocarbon, such as pentane, hexane or cyclohexane, or an aromatic hydrocarbon, such as toluene, xylene, cumene and the like, or in a mixture of the abovementioned solvents. The reaction of compound II with compound III (or compound IIIa) is customarily carried out in the presence of an auxiliary base. Suitable bases are inorganic bases, such as sodium carbonate or potassium carbonate, or sodium hydrogen carbonate or potassium hydrogen carbonate, and organic bases, for example trialkylamines, such as triethylamine, or pyridine compounds, such as pyridine, lutidine, 4-dimethylamino-pyridine and the like. The latter compounds can at the same time serve as solvents. The auxiliary base is customarily employed in at least equimolar quantities, based on the amine compound II.

The reaction of compound II with compound III or IIIa, respectively yields compound IV or IVa, respectively, which, in case $R^a$ is a N-protecting group, is deprotected to yield the compound of the general formula I or I', wherein $R^1$ is hydrogen. Deprotection of the compound IV or IVa, respectively, can be achieved by standard methods, e.g. by the methods as described in P. J. Kocienski "Protecting Groups", $2^{nd}$ ed., Georg Thieme Verlag, Stuttgart 2000, pp 186-237 and in the literature cited therein.

Customary methods can then be used to react these compounds with a methylating agent such as methyliodide or dimethylsulfate resulting in a compound I or I', respectively, in which $R^1$ methyl. The reaction conditions which are required for this methylating reaction are disclosed, for example, in WO 02/083652, Tetrahedron 2000, 56(38) pp. 7553-7560 and Synlett. 2000 (4), pp. 475-480.

For preparing a compound of formula I or I', respectively, in which $R^1$ is methyl, it is likewise possible to react a compound of formula I or I', in which $R^1$ is hydrogen, with formaldehyde in the presence of a reducing agent in a sense of a reductive amination. Suitable reducing agents are borohydrides such as sodium borohydride, sodium cyanoborohydride, sodium triacetoxyborohydride or borane-pyridine. The reductive amination is usually carried out in an organic solvent such as dichloromethane, 1,2-dichloroethane, tetrahydrofuran or acetonitrile.

Reaction of the compound IV or IVa with an alkylating agent yields a compound of the formula IV or IVa, respectively, wherein $R^a$, $R^2$, $R^3$, $R^5$ and $R^6$ are as defined above. In the compound of the formula IV' or IV'a, respectively, the sulfonamide hydrogen is replaced by $C_1$-$C_4$ alkyl, $C_3$-$C_4$ cycloalkyl, $C_3$-$C_4$ cycloalkylmethyl or fluorinated $C_1$-$C_4$ alkyl.

It is possible to react the compound IV or IVa with a methylating agent such as methyliodide or dimethylsulfate to yield a compound of the formula IVb or IVc, respectively, wherein $R^a$, $R^2$, $R^3$, $R^5$ and $R^6$ are as defined above.

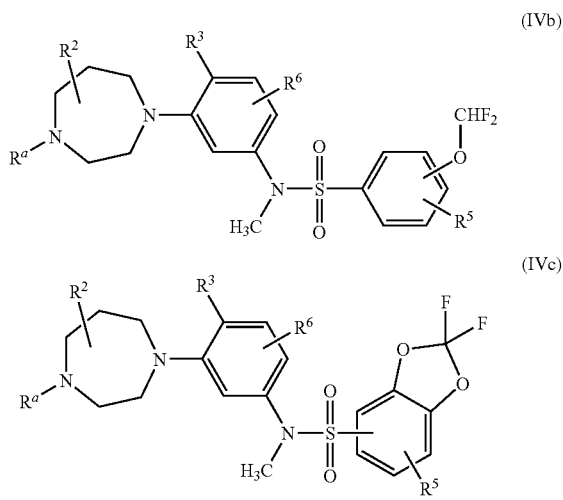

If $R^a$ in formulae IVb or IVc is an N-protecting group, compound IVb or IVc, respectively, is deprotected to yield the compound of the general formula I, wherein $R^1$ is hydrogen. Deprotection of the compound IVb or IVc can be achieved by standard methods, e.g. by the methods as described in P. J. Kocienski "Protecting Groups", $2^{nd}$ ed., Georg Thieme Verlag, Stuttgart 2000, pp 186-237, and in the literature cited therein.

The compounds of the general formula II are known per se or can be prepared in the manner shown in scheme 2.

Scheme 2:

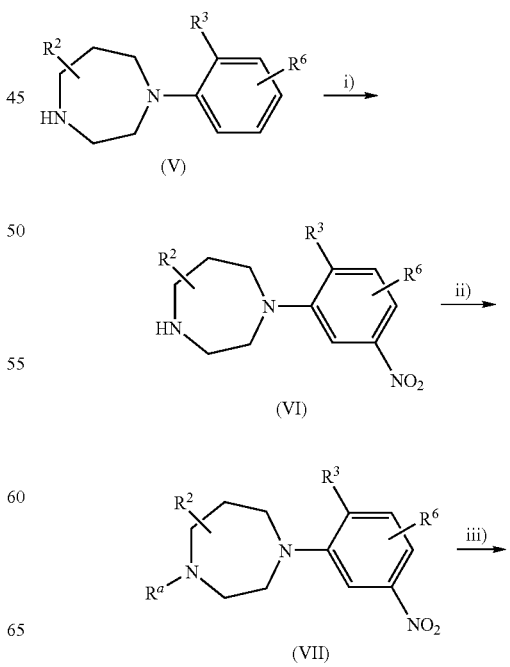

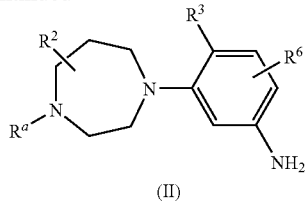

(II)

In scheme 2, $R^a$, $R^2$, $R^3$ and $R^6$ have the previously mentioned meanings.

In step i) of scheme 2, the compound V is subjected to a nitration under standard conditions thereby yielding compound VI. Reaction conditions can be taken e.g. from U.S. Pat. No. 6,599,904 or from the working examples of the present application.

In step ii) of scheme 2, the NH-group of compound VI is protected, either by a conventional N-protecting group as defined above or by introducing a methyl group via a methylating agent such as methyl bromide, methyl iodide or dimethylsulfate. Introduction of an N-protecting group into compound VI can be achieved by standard methods, e.g. by the methods as described in P. J. Kocienski "Protecting Groups", $2^{nd}$ ed., Georg Thieme Verlag, Stuttgart 2000, pp 186-237, and in the literature cited therein. Methylation of compound VI is likewise achieved by standard methods of organic chemistry.

In step iii), the nitro group in compound VII is reduced to the $NH_2$ group to yield compound II. The reaction conditions which are required for step iii) correspond to the customary conditions for reducing aromatic nitro groups which have been described extensively in the literature (see, for example, J. March, Advanced Organic Chemistry, 3rd ed., J. Wiley & Sons, New-York, 1985, p. 1183, and the literature cited in this reference). The reduction can be achieved, for example, by reacting the nitro compound VII with a metal such as iron, zinc or tin under acidic reaction conditions, i.e. using nascent hydrogen, or using a complex hydride such as lithium aluminum hydride or sodium borohydride, preferably in the presence of transition metal compounds of nickel or cobalt such as $NiCl_2(P(phenyl)_3)_2$, or $CoCl_2$, (see Ono et al. Chem. Ind. (London), 1983 p. 480), or using $NaBH_2S_3$ (see Lalancette et al. Can. J. Chem. 49, 1971, p. 2990), with it being possible to carry out these reductions, depending on the given reagent, in substance or in a solvent or diluent. Alternatively, the reduction of VII to II can be carried out with hydrogen in the presence of a transition metal catalyst, e.g. using hydrogen in the presence of catalysts based on platinum, palladium, nickel, ruthenium or rhodium. The catalysts can contain the transition metal in elemental form or in the form of a complex compound, of a salt or of an oxide of the transition metal, with it being possible, for the purpose of modifying the activity, to use customary coligands, e.g. organic phosphine compounds, such as triphenylphosphines, tricyclohexylphosphines or tri-n-butylphosphines or phosphites. The catalyst is customarily employed in quantities of from 0.001 to 1 mol per mol of compound VII, calculated as catalyst metal. In a preferred variant, the reduction is effected using tin(II) chloride in analogy with the methods described in Bioorganic and Medicinal Chemistry Letters 2002, 12(15), pp. 1917-1919, and in Journal of Medicinal Chemistry 2002, 45(21), pp. 4679-4688. The reaction of VII with tin(II) chloride is preferably carried out in an inert organic solvent, preferably an alcohol such as methanol, ethanol, isopropanol or butanol.

The compounds of the general formula VI are known per se or can be prepared according to the following synthetic scheme 3.

Scheme 3:

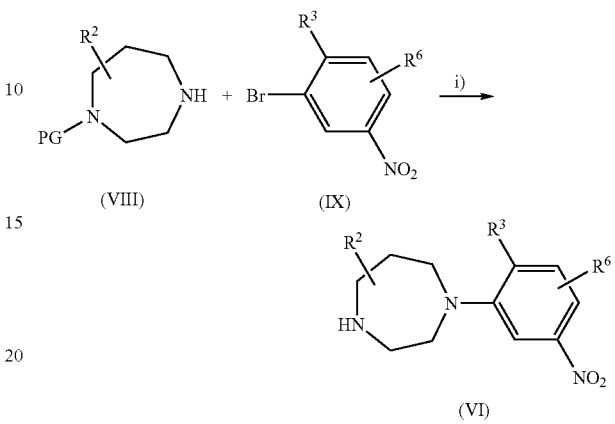

In scheme 3, $R^2$, $R^3$ and $R^6$ have the previously mentioned meanings. PG is hydrogen or a nitrogen protecting group.

In step i) of scheme 3, a bromo-nitro benzene compound IX and an optionally protected (homo)piperazine derivative VIII, both of which are either commercially available or prepared following established synthetic procedures, are coupled via Pd-catalyzed Buchwald-Hartwig reaction, yielding directly or after deprotection, respectively, a compound VI.

The compounds of the formula IX, wherein $R^3$ is difluoromethoxy can be prepared by reacting commercially available 2-bromo-4-nitrophenol with 2-chloro-2,2-difluoro-acetophenone by analogy to the method described in J. Hu et al., Journal of Organic Chemistry, 2006, 71, 9845-9848, to yield 2-bromo-1-difluoromethoxy-4-nitro-benzene, which is then converted into the compound of the formula II with $R^3$ being difluoromethoxy by analogy to the methods depicted in schemes 2 and 3.

The compounds of the formula II, wherein $R^3$ is methoxy and $R^6$ is fluorine, can also be prepared according to scheme 3 from the commercially available 1-bromo-2-methoxy-5-nitrobenzene via Pd-catalyzed Buchwald-Hartwig coupling with e.g. a protected homopiperazine derivative and subsequent reduction of the nitro group to the amino group as described for step iii) in scheme 2.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. and p. 9225 ff. and also, in a general manner, "Microwaves in Organic Synthesis", André Loupy (Ed.), Wiley-VCH 2002.

The acid addition salts of compounds I and I' are prepared in a customary manner by mixing the free base with a corresponding acid, where appropriate in solution in an organic solvent, for example acetonitrile, a lower alcohol, such as methanol, ethanol or propanol, an ether, such as diethyl ether, methyl tert-butyl ether or diisopropyl ether, a ketone, such as acetone or methyl ethyl ketone, an ester, such as ethyl acetate, mixtures thereof as well as mixtures thereof with water.

The compounds of the present invention can be a 5-HT$_6$ receptor agonist, including partial agonistic activity, or a 5-HT$_6$ receptor antagonist, including inverse agonist activity.

The compounds of formulae I and I' according to the present invention, as well as their salts and their N-oxides, have a surprisingly high affinity for 5-HT$_6$ receptors. The high affinity of the compounds according to the invention for 5-HT$_6$ receptors is reflected in very low in-vitro receptor binding constants ($K_i$(5-HT$_6$) values) of as a rule less than 250 nM (nmol/l), frequently of less than 100 nM, preferably of less than 50 nM, in particular of less than 10 nM, and specifically of less than 5 nM. The displacement of $^3$H-LSD can, for example, be used in receptor binding studies for determining binding affinities to 5-HT$_6$ receptors.

Furthermore the compounds of formulae I and I', as well as their salts and their N-oxides, are selective 5-HT$_6$ receptor ligands which, because of their low affinity for other receptors such as dopamine receptors, adrenergic receptors, muscarinic receptors, histamine receptors, opiate receptors, in particular dopamine D$_2$, α$_1$-adrenergic and histamine H$_1$ receptors, give rise to fewer side-effects than other, less selective 5-HT$_6$ ligands.

For instance the 5-HT$_6$/D$_2$, 5-HT$_6$/α$_1$-adrenergic or 5-HT$_6$/H$_1$ selectivities of the compounds according to the present invention, i.e. the ratios $K_i$(D$_2$)/$K_i$(5-HT$_6$), $K_i$(α$_1$-adrenergic)/$K_i$(5-HT$_6$) or $K_i$(H$_1$)/$K_i$(5-HT$_6$) of the receptor binding constants, is as a rule at least 10, frequently at least 25, preferably at least 50, even better at least 100.

The displacement of [$^3$H]SCH23390 or [$^{125}$I]spiperone can be used, for example, for carrying out receptor binding studies on D$_1$, D$_2$ and D$_4$ receptors.

Furthermore the compounds of the present invention because of their structural features are susceptible to display an enhanced brain penetration than other known 5-HT$_6$ receptor ligands.

Because of their binding profile, the compounds of the present invention can be used for treating diseases which respond to 5-HT$_6$ receptor ligands (or which are susceptible to treatment with a 5-HT$_6$ receptor ligand), i.e. they are effective for treating those medical disorders or diseases in which exerting an influence on (modulating) the 5-HT$_6$ receptors leads to an improvement in the clinical picture or to the disease being cured. Examples of these diseases are disorders or diseases of the central nervous system.

Disorders or diseases of the central nervous system are understood as meaning disorders which affect the spinal cord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are in particular disorders which respond to a modulation of the 5-HT$_6$ receptor. They include cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, addiction diseases including e.g. drug addiction and obesity.

The addiction diseases include psychic disorders and behavioral disturbances which are caused by the abuse of psychotropic substances, including certain pharmaceuticals, such as sedative, anxiolytica, hypnotics or narcotics (hereinafter also referred to as drug addiction), and also other addiction diseases, such as addiction to gaming (gambling; impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come more particularly into consideration are opioids, cocaine, amphetamine or amphetamine-like substances, hallucinogens, NMDA-receptor antagonists such phencyclidine and related cyclidines, dextrometorphan, dextrorphan, ibogaine, ketimine and tiletamine, cannabis, nicotine and alcohol. Other addiction diseases include gaming (gambling), including problem gambling (compulsive gambling, ludomania), computer or video game addiction and internet addiction.

With regard to the treatment of addiction diseases, particular preference is given to those compounds according to the present invention which themselves do not possess any psychotropic effect. This can also be observed in a test using rats, which, after having been administered compounds which can be used in accordance with the invention, reduce their self administration of psychotropic substances, for example cocaine or alcohol.

According to another aspect of the present invention, the compounds according to the invention are suitable for treating disorders whose causes can at least partially be attributed to an anomalous activity of 5-HT$_6$ receptors.

According to another aspect of the present invention, the treatment is directed, in particular, toward those disorders which can be influenced, within the sense of an expedient medicinal treatment, by the binding of preferably exogenously administered binding partners (ligands) to 5-HT$_6$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds of the present invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

The compounds according to the invention are preferentially suitable for treating diseases of the central nervous system, more preferably for treating cognitive dysfunctions and in particular, for treating cognitive dysfunctions associated with schizophrenia or with Alzheimer's disease.

According to another aspect of the invention the compounds of the present invention are particularly suitable for treating addiction diseases caused for instance by the abuse of psychotropic substances, such as pharmaceuticals, narcotics, nicotine or alcohol, including psychic disorders and behavioral disturbances related thereto. The compounds of the present invention are likewise particularly suitable for treating addiction diseases which are not caused by the abuse of psychotropic substances, such as gaming (gambling), including problem gambling (compulsive gambling, ludomania), computer or video game addiction and internet addiction. With regard to addiction diseases, the compound of the present invention can be used for the therapy during addiction and also for preventing relapse into addiction.

According to another aspect of the invention the compounds of formulae (I) and (I)', their salts and their N-oxides are particularly suitable for treating nutritional disorders, such as obesity, as well as diseases related thereto, such as cardiovascular diseases, digestive diseases, respiratory diseases, cancer or type 2 diabetes.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the compounds of formulae I or I', their salts and/or their N-oxides are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Kantor-Verlag, 1996.

The following examples serve to explain the present invention without limiting its scope.

The compounds were either characterized via proton-NMR in $d_6$-dimethylsulfoxid or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

I. Preparation of the Intermediate Compounds IV

Preparation Example 1

4-[5-(3-Difluoromethoxy-benzenesulfonylamino)-2-methoxy-phenyl]-[1,4]diazepane-1-carboxylic acid tert-butyl ester 1.1 4-(5-Nitro-2-methoxy-phenyl)-[1,4]diazepane-1-carboxylic acid tert-butyl ester A suspension of 0.64 g of palladium acetate (2.85 mmol) and 1.77 g BINAP (2,2'-bis(diphenylphosphino)-1,1'-binaphthyl) (2.85 mmol) was heated to 75° C. for 10 min and then added dropwise to a solution of 5 g of tert-butyl 1,4-diazepane-1-carboxylate (24.97 mmol) and 3.43 g of sodium tert-butoxide (35.7 mmol) in 200 mL of toluene at 75° C. Stirring was continued for 3 h at 75° C. and 18 h at room temperature. The reaction mixture was filtered over Celite, the filtrate evaporated to dryness under reduced pressure, the residue dissolved in dichloromethane and the organic phase washed with water and saturated aqueous sodium chloride. The combined organic phases were dried over sodium sulphate, filtered, the solvents removed in vacuo and the residue purified via silica gel chromatography with cyclohexane/ethyl acetate to yield 4.5 g of the title product.

1.2 4-(5-Amino-2-methoxy-phenyl)-[1,4]diazepane-1-carboxylic acid tert-butyl ester 4.5 g of 4-(5-nitro-2-methoxy-phenyl)-[1,4]diazepane-1-carboxylic acid tert-butyl ester (12.8 mmol) was dissolved in 40 mL of methanol, 1.36 g of 10% Pd/C was added and the mixture was hydrogenated under hydrogen gas for 4 h at 40° C. The reaction mixture was filtered over Celite and the filtrate evaporated to dryness in vacuo to yield 3.9 g of the title compound which was used in the next step without further purification.

1.3 4-[5-(3-Difluoromethoxy-benzenesulfonylamino)-2-methoxy-phenyl]-[1,4]diazepane-1-carboxylic acid tert-butyl ester 0.5 g of 4-(5-amino-2-methoxy-phenyl)-[1,4]diazepane-1-carboxylic acid tert-butyl ester (1.556 mmol) was reacted as described for Preparation example 1 with 3-(difluoromethoxy)-benzene-sulfonylchloride to yield 0.64 g of the title compound.

II. Preparation of the Compounds I

Example 1

N-(3-[1,4]Diazepan-1-yl-4-methoxy-phenyl)-3-difluoromethoxy-benzenesulfonamide hydrochloride

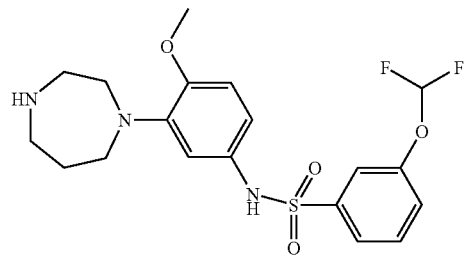 [SMILES: COc1ccc(NS(=O)(=O)c2cccc(OC(F)F)c2)cc1N1CCCNCC1]

0.64 g of 4-[5-(3-difluoromethoxy-benzenesulfonylamino)-2-methoxy-phenyl]-[1,4]diazepane-1-carboxylic acid tert-butyl ester (1.213 mmol) were dissolved in 20 mL of dichloromethane and 1.82 mL of a 2N solution of hydrochloric acid in diethyl ether was added. After stirring at room temperature for 16 h, the solvents were evaporated, the residue redissolved in water, the aqueous phase washed with dichloromethane and then lyophilized to yield the title compound.

ESI-MS: 428.1 [M+H]$^+$;
$^1$H-NMR (DMSO-$d_6$, 400 Hz): δ [ppm] 9.95 (s, 1H), 8.85 (s broad, 2H), 7.6 (m, 2H), 7.45 (m, 2H), 7.3 (t, 1H), 6.8 (d, 1H), 6.6 (s, 1H), 6.55 (d, 1H), 3.7 (s, 3H), 3.2 (m, 6H), 3.1 (m, 2H), 2.05 (m, 2H).

Example 2

3-Difluoromethoxy-N-[4-methoxy-3-(4-methyl-[1,4]diazepan-1-yl)-phenyl]-benzenesulfonamide hydrochloride

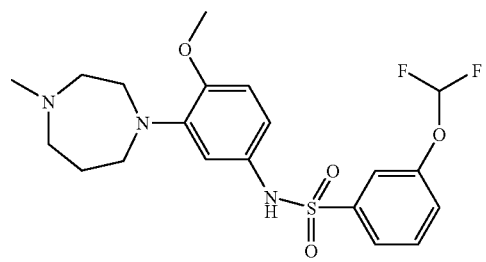 [SMILES: COc1ccc(NS(=O)(=O)c2cccc(OC(F)F)c2)cc1N1CCCN(C)CC1]

The title compound was prepared from the title compound of Example 1 under reductive amination conditions employing an aqueous solution of formaldehyde and sodium borohydride in acetonitrile as solvent.

ESI-MS: 442.1 [M+H]$^+$;
$^1$H-NMR (DMSO-$d_6$, 400 Hz): δ [ppm] 11.1 (s broad, 1H), 10.1 (s, 1H), 7.55-7.65 (m, 2H), 7.5 (s, 1H), 7.4 (d, 1H), 7.3 (t, 1H), 6.8 (d, 1H), 6.65 (s, 1H), 6.6 (d, 1H), 3.7 (s, 3H), 3.1-3.5 (several m, 7H), 2.95 (m, 1H), 2.75 (d, 3H), 2.3 (m, 1H), 2.15 (m, 1H).

Example 3

N-(3-[1,4]Diazepan-1-yl-4-methoxy-phenyl)-2-difluoromethoxy-benzenesulfonamide hydrochloride

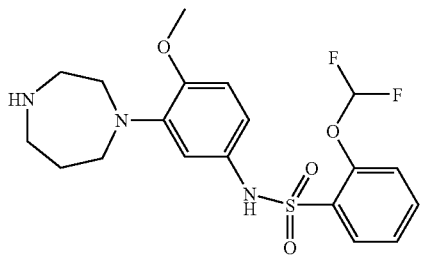 [SMILES: COc1ccc(NS(=O)(=O)c2ccccc2OC(F)F)cc1N1CCCNCC1]

The title compound was prepared in a manner analogous to the above described preparation of Example 1.

ESI-MS: 428.1 [M+H]+;

$^1$H-NMR (DMSO-$d_6$, 400 Hz): δ [ppm] 9.9 (s, 1H), 8.8 (s broad, 2H), 7.8 (d, 1H), 7.65 (m, 1H), 7.3-7.4 (m, 2H), 7.3 (t, 1H), 6.8 (d, 1H), 6.65 (s, 1H), 6.6 (d, 1H), 3.2 (broad, 6H), 3.05 (m, 2H), 2.05 (m, 2H).

Example 4

2-Difluoromethoxy-N-[4-methoxy-3-(4-methyl-[1,4]diazepan-1-yl)-phenyl]-benzenesulfonamide hydrochloride

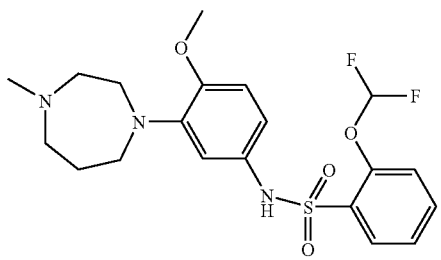 [SMILES: COc1ccc(NS(=O)(=O)c2ccccc2OC(F)F)cc1N1CCCN(C)CC1]

The title compound was prepared from the title compound of Example 3 under reductive amination conditions employing an aqueous solution of formaldehyde and sodium borohydride in acetonitrile as solvent.

ESI-MS: 442.1 [M+H]+;

$^1$H-NMR (DMSO-$d_6$, 400 Hz): δ [ppm] 11.25 (s broad, 1H), 10.0 (s, 1H), 7.8 (d, 1H), 7.65 (m, 1H), 7.25-7.4 (several m, 3H), 6.8 (d, 1H), 6.75 (s, 1H), 6.65 (d, 1H), 3.7 (s, 3H), 3.4 (m, 3H), 3.3 (m, 3H), 3.2 (m, 1H), 3.0 (m, 1H), 2.75 (d, 3H), 2.35 (m, 1H), 2.15 (m, 1H).

Example 5

N-(3-[1,4]Diazepan-1-yl-4-methyl-phenyl)-2-difluoromethoxy-benzenesulfonamide hydrochloride

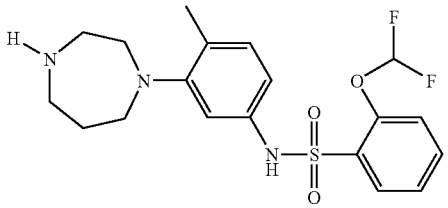 [SMILES: Cc1ccc(NS(=O)(=O)c2ccccc2OC(F)F)cc1N1CCCNCC1]

The title compound was prepared in analogy to the preparation of Example 1.

ESI-MS: 412.1 [M+H]+

$^1$H-NMR (DMSO-$d_6$, 400 Hz): δ [ppm] 10.2 (s, 1H), 9.55 (broad, 2H), 7.87 (d, 1H), 7.65 (m, 1H), 7.35 (m, 2H), 7.3 (t, 1H), 6.95 (d, 1H), 6.85 (s, 1H), 6.7 (d, 1H), 3.1-3.3 (m, 6H), 2.95 (m, 2H), 2.1 (s, 3H), 2.0 (m, 2H).

Example 6

N-(3-[1,4]Diazepan-1-yl-4-methyl-phenyl)-3-difluoromethoxy-N-methyl-benzenesulfonamide hydrochloride

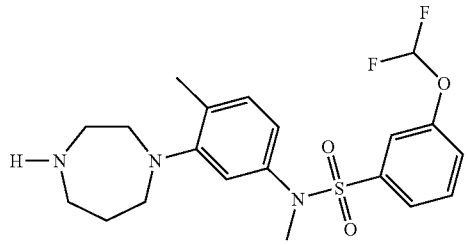 [SMILES: Cc1ccc(N(C)S(=O)(=O)c2cccc(OC(F)F)c2)cc1N1CCCNCC1]

The title compound was prepared from 4-[5-(3-difluoromethoxy-benzenesulfonylamino)-2-methyl-phenyl]-[1,4]diazepane-1-carboxylic acid tert-butyl ester which was prepared in manner analogous to the preparation of the title compound of Preparation Example 2, employing as alkylating agent methyl iodide in the presence of sodium hydride, followed by removing the amino-protecting group Boc.

ESI-MS: 426.1 [M+H]+

$^1$H-NMR (DMSO-$d_6$, 400 Hz): δ [ppm] 9.75 (broad, 2H), 7.77 (m, 1H), 7.55 (m, 1H), 7.4 (d, 1H), 7.3 (t, 1H), 7.23 (m, 1H), 7.12 (d, 1H), 6.75 (s, 1H), 6.7 (d, 1H), 4.05 (m, 2H), 3.15-3.5 (several m, 8H), 3.13 (s, 3H), 2.95 (m, 2H), 2.25 (s, 3H), 2.0 (m, 2H).

Example 7

N-(3-[1,4]Diazepan-1-yl-4-methyl-phenyl)-3-difluoromethoxy-benzenesulfonamide hydrochloride

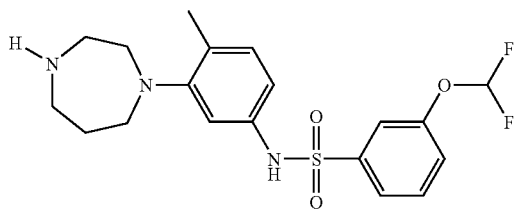 [SMILES: Cc1ccc(NS(=O)(=O)c2cccc(OC(F)F)c2)cc1N1CCCNCC1]

The title compound was prepared in analogy to the preparation of Example 3.

ESI-MS: 412.1 [M+H]$^+$ $^1$H-NMR (DMSO-d$_6$, 400 Hz): δ [ppm] 10.3 (s, 1H), 9.5 (broad, 2H), 7.6 (m, 2H), 7.52 (s, 1H), 7.4 (m, 1H), 7.3 (t, 1H), 7.0 (d, 1H), 6.85 (s, 1H), 6.7 (d, 1H), 3.1-3.3 (several m, 6H), 2.95 (m, 2H), 2.1 (s, 3H), 2.0 (m, 2H).

Example 8

2-Difluoromethoxy-N-[4-methyl-3-(4-methyl-[1,4]diazepan-1-yl)-phenyl]-benzenesulfonamide hydrochloride

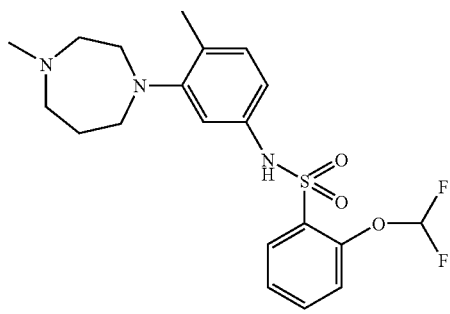 [SMILES: Cc1ccc(NS(=O)(=O)c2ccccc2OC(F)F)cc1N1CCCN(C)CC1]

The title compound was prepared in analogy to the preparation of Example 4.

ESI-MS: 426.2 [M+H]$^+$ $^1$H-NMR (DMSO-d$_6$, 400 Hz): δ [ppm] 10.8 (broad, 1H), 10.15 (broad, 1H), 7.87 (d, 1H), 7.65 (m, 1H), 7.35 (m, 2H), 7.28 (t, 1H), 6.95 (d, 1H), 6.83 (s, 1H), 6.67 (d, 1H), 3.1-3.6 (m, 6H), 2.95 (m, 2H), 2.8 (s, 3H), 2.2 (s, 3H), 2.0-2.2 (m, 2H).

III. Biological Investigations

Displacement of radioligands binding to the following cloned human receptors

1. Preparation of Membranes by Ultrasonic Treatment and Differential Centrifugation Cells from stable clonal cell lines expressing the corresponding receptor (5-HT$_6$, α$_1$-adrenergic, dopamine D$_2$ or histamine H$_1$ receptors) were washed with PBS (w/o Ca$^{++}$, Mg$^{++}$) and harvested in PBS with 0.02% EDTA. The cells were collected by centrifugation at 500 g for 10 min at 4° C., washed with PBS and centrifuged (500 g, 10 min, 4° C.). The pellets were stored at −80° C. until use. For membrane preparation, the thawed cell pellet was resuspended in ice-cold sucrose buffer (0.25 M sucrose, 10 mM Hepes (pH 7.4), 1 mM Phenylmethylsulfonyl fluoride (PMSF) in DMSO, 5 µg/ml Pepstatin-A, 3 mM EDTA, 0.025% Bacitracin) and homogenized with a Branson Sonifier W-250 (Settings: Timer 4; Output Control 3; Duty Cycle constant; 2 to 3 cycles). Cell disruption was checked with the aid of a microscope. Remaining unbroken cells were pelleted at 1.000 g for 10 min at 4° C. The sucrose buffer supernatant was then centrifuged at 60.000 g for 1 h at 4° C. (Beckman Ultrazentrifuge XL 80). The pellet was resuspended in 30 ml ice-cold Tris buffer (20 mM TRIS (pH 7.4), 5 µg/ml Pepstatin A, 0.1 mM PMSF, 3 mM EDTA) by pipetting through a 10 ml serological pipet and centrifuged for 1 h at 4° C. at 60.000 g. A final resuspension was performed in a small volume of ice-cold Tris buffer (see above) by pressing through a serological pipet followed by ultrasonic treatment with a Branson Sonifier W-250 (Settings: Timer 1; Output Control 3; Duty Cycle constant; 1 cycle). Protein concentration was determined (BCA-Kit; Pierce) and aliquots stored at −80° C. or in liquid nitrogen for long-term storage.

2. Receptor Binding Experiments

All receptor binding experiments were carried out in the corresponding assay buffer in a total volume of 200 µl in the presence of various concentrations of test compound (10$^{-5}$ M to 10$^{-9}$ M, tenfold serial dilution, duplicate determinations). The assays were terminated by filtration on polyethylenimine (PEI 0.1% or 0.3%) presoaked Packard Unifilter Plates (GF/C or GF/B) with a Tomtec MachIII U 96 well-plate harvester. After the plates had been dried for 2 h at 55° C. in a drying chamber scintillation cocktail (BetaPlate Scint; PerkinElmer) was added. Radioactivity was measured in a Microbeta Trilux two hours after the addition of the scintillation mixture. Data derived from liquid scintillation counting were analysed by iterative non-linear regression analysis with the use of the Statistical Analysis System (SAS): a program similar to "LIGAND" as described by Munson and Rodbard (Analytical Biochemistry 107, 220-239 (1980).

a) 5-HT$_6$ Receptor Binding Assay

HEK293 cells stably expressing the h-5-HT$_6$ receptor (NCBI Reference Sequence XM 001435) were cultured in RPMI1640 medium supplemented with 25 mM HEPES, 10% fetal calf serum and 1-2 mM glutamine. The membrane preparation was performed as described in section 1. For these membranes a K$_D$ of 1.95 nM for [$^3$H]-LSD (Lysergic Acid Diethylamide; Amersham, TRK1038) was determined by means of saturation binding experiments. On the day of the assay, the membranes were thawed, diluted in assay buffer (50 mM Tris-HCl, 5 mM CaCl$_2$, 0.1% ascorbic acid, 10 µM pargyline, pH 7.4) to a concentration of 8 µg protein/assay and homogenized by gentle vortexing For inhibition studies, 1 nM [$^3$H]-Lysergic Acid Diethylamide was incubated in the presence of various concentrations of test compound in assay buffer. Non-specific binding was defined with 1 µM methiothepin. The binding reaction was carried out for 3.5 h at room temperature. During the incubation, the plates were shaken on a plate shaker at 100 rpm and terminated by filtration on Packard Unifilter GF/C (0.1% PEI) plates, followed by 2 wash cycles with ice-cold 50 mM Tris-HCl, 5 mM CaCl$_2$.

b) Dopamine D$_2$ Receptor Binding Assay

HEK293 cells stably expressing the dopamine D$_2$ receptor (NCBI Reference Sequence NM_000795) were cultured in RPMI1640 medium supplemented with 25 mM HEPES, 10% fetal calf serum and 1-2 mM glutamine. The membrane preparation was performed as described in section 1. For these membranes a K$_D$ of 0.22 nM for [$^{125}$I]-iodospiperone (PerkinElmer Life Sciences, NEX284) was determined by means of saturation binding experiments. On the day of the assay, the membranes were thawed, diluted in assay buffer (50 mM Tris-HCl, 120 mM NaCl, 5 mM $MgCl_2$, 5 mM KCl, 1.5 mM $CaCl_2$, pH 7.4) to a concentration of 15 μg protein/assay and homogenized by gentle vortexing. For inhibition studies, 0.01 nM [$^{125}$I]-iodospiperone (PerkinElmer Life Sciences, NEX284) was incubated in the presence of various concentrations of test compound in assay buffer. Non-specific binding was defined with 1 μM haloperidol. The binding reaction was carried out for 1 h at room temperature and terminated by filtration on Packard Unifilter GF/B (0.1% PEI) plates, followed by 6 wash cycles with an ice-cold 7% polyethylenglycol solution.

c) $α_1$-Adrenergic Receptor Binding Assay

CHO-$K_1$ cells stably expressing the $α_1$-adrenergic receptor (NCBI Reference Sequence NM_033303) were cultured in RPMI1640 medium supplemented with 25 mM HEPES, 10% fetal calf serum and 1-2 mM glutamine. The membrane preparation was performed as described in section 1. For these membranes a $K_D$ of 0.12 nM for [$^3$H]-prazosine (PerkinElmer Life Sciences, NET823) was determined by means of saturation binding experiments. On the day of the assay, the membranes were thawed, diluted in assay buffer (50 mM Tris-HCl, pH 7.4) to a concentration of 4 μg protein/assay and homogenized by gentle vortexing. For inhibition studies, 0.1 nM [$^3$H]-prazosine (PerkinElmer Life Sciences, NET823) was incubated in the presence of various concentrations of test compound in assay buffer. Non-specific binding was defined with 1 μM phentolamine. The binding reaction was carried out for 1 h at room temperature and terminated by filtration on Packard Unifilter GF/C (0.1% PEI) plates, followed by 3 wash cycles with ice-cold assay buffer.

d) $H_1$ Receptor Binding Assay

CHO-$K_1$ cells stably expressing the histamine $H_1$ receptor (Euroscreen-ES-390-C, NCBI Reference Sequence NM_000861) were cultured in RPMI1640 medium supplemented with 25 mM HEPES, 10% fetal calf serum and 1-2 mM glutamine. The membrane preparation was performed as described in section 1. For these membranes a $K_D$ of 0.83 nM for [$^3$H]-pyrilamine (PerkinElmer Life Sciences, NET594) was determined by means of saturation binding experiments. On the day of the assay, the membranes were thawed, diluted in assay buffer (50 mM $Na_2HPO_4$, 50 mM $KH_2PO_4$, pH 7.4) to a concentration of 6 μg protein/assay and homogenized by gentle vortexing. For inhibition studies, 1 nM [$^3$H]-pyrilamine (PerkinElmer Life Sciences, NET594) was incubated in the presence of various concentrations of test compound in assay buffer. Non-specific binding was defined with 1 μM pyrilamine. The binding reaction was carried out for 50 minutes at room temperature and terminated by filtration on Packard Unifilter GF/C (0.3% PEI) plates, followed by 2 wash cycles with ice-cold assay buffer.

3. Data Analysis

Data derived from liquid scintillation counting were analyzed by iterative non-linear regression analysis with the use of the Statistical Analysis System (SAS): a program similar to "LIGAND" as described by Munson and Rodbard (Anal. Biochem. 1980, 107, 220-239). Fitting was performed according to formulae described by Feldman (Anal. Biochem. 1972, 48, 317-338). $IC_{50}$, nH and $K_i$ values were expressed as geometrical mean. For receptors with a low affinity for the test compound, where the highest tested compound concentration inhibited less than 30% of specific radioligand binding, $K_i$-values were determined according to the equation of Cheng and Prusoff (Biochem. Pharmacol. 1973, 22, 2099-2108) and expressed as greater than (>).

The results of the receptor binding studies are expressed as receptor binding constants $K_i$(5-$HT_6$), $K_i$($D_2$), $K_i$($α_1$-adrenergic) and $K_i$($H_1$), respectively, as described herein before, and given in table I.

In these tests, the compounds according to the invention exhibit very good affinities for the 5-$HT_6$ receptor ($K_i$<250 nM or <50 nM or <20 nM and frequently <10 nM). Furthermore those compounds bind selectively to the 5-$HT_6$ receptor, as compared to the affinity for the $D_2$, the $α_1$-adrenergic or the $H_1$ receptors. These compounds exhibit little affinities for the $D_2$, $α_1$-adrenergic or $H_1$ receptors ($K_i$>250 nM or >1000 nM and frequently >10000 nM).

Example 1: Ki (5$HT_6$)<10 nM
Example 3: Ki (5$HT_6$)<10 nM
Example 5: Ki (5$HT_6$)<50 nM
Example 6: Ki (5$HT_6$)<250 nM
Example 7: Ki (5$HT_6$)<50 nM
Example 8: Ki (5$HT_6$)<10 nM 4. Determination of the Metabolic Stability The metabolic stability of the compounds of the invention was determined in the following assay by analyzing the microsomal half-life. The test substances are incubated in a concentration of 0.5 μM as follows:

0.5 μM test substance is preincubated together with liver microsomes of various species (0.25 mg of protein/ml) in 0.05 M potassium phosphate buffer pH 7.4 in microtiter plates at 37° C. for 5 min. The reaction is started by adding NADPH (1 mg/mL). Aliquots are taken after 0, 5, 10, 15, 20 and 30 min, and the reaction is stopped with the same volume of acetonitrile and cooled down. The remaining test compound concentrations are being determined by liquid chromatography-mass spectrometry analysis. Intrinsic clearance values are calculated using the elimination rate constant of test compound depletion.

We claim:
1. A benzenesulfonanilide compound of formulae I or I'

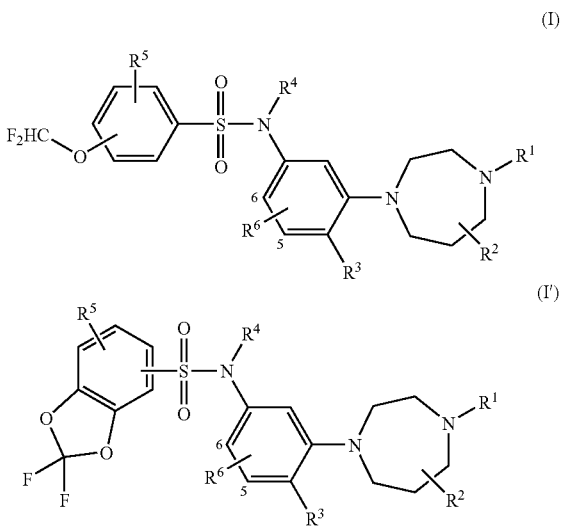

wherein
$R^1$ is hydrogen or methyl;
$R^2$ is hydrogen or methyl;
$R^3$ hydrogen, $C_1$-$C_3$ alkyl, halogen, $C_1$-$C_3$ alkoxy, fluorinated $C_1$-$C_3$ alkyl or fluorinated $C_1$-$C_3$ alkoxy;
$R^4$ is hydrogen, $C_1$-$C_4$ alkyl, $C_3$-$C_4$ cycloalkyl, $C_3$-$C_4$ cycloalkylmethyl or fluorinated $C_1$-$C_4$ alkyl;

R⁵ is hydrogen, fluorine, chlorine, $C_1$-$C_4$ alkyl, fluorinated $C_1$-$C_4$ alkyl, $C_1$-$C_4$ alkoxy or fluorinated $C_1$-$C_4$ alkoxy; and R⁶ is hydrogen, fluorine or chlorine;
wherein R² is positioned vicinal to the radical R¹;
and physiologically tolerated acid addition salts and the N-oxides thereof.

2. The compound of claim 1, wherein R¹ is hydrogen.
3. The compound of claim 1, wherein R¹ is methyl.
4. The compound of claim 1, wherein R² is hydrogen.
5. The compound of claim 1, wherein R² is methyl.
6. The compound of claim 5, wherein the carbon atom that carries R² has S-configuration.
7. The compound of claim 5, wherein the carbon atom that carries R² has R-configuration.
8. The compound of claim 1, wherein R³ is hydrogen, halogen, $C_1$-$C_3$ alkoxy, fluorinated $C_1$-$C_3$ alkyl or fluorinated $C_1$-$C_3$ alkoxy.
9. The compound of claim 1, wherein R³ is $C_1$-$C_3$ alkyl.
10. The compound of claim 8, wherein R³ is methoxy.
11. The compound of claim 8, wherein R³ is hydrogen or fluorine.
12. The compound of claim 1, wherein R⁴ is hydrogen or $C_1$-$C_3$ alkyl.
13. The compound of claim 1, wherein R⁵ is hydrogen.
14. The compound of claim 1, wherein R⁵ is methyl, methoxy or difluoromethoxy.
15. The compound of claim 1, wherein R⁶ is hydrogen.
16. The compound of claim 1, wherein R⁵ and R⁶ are hydrogen, R³ is selected from the group consisting of $C_1$-$C_3$ alkoxy and fluorinated $C_1$-$C_2$ alkoxy and R⁴ is selected from the group consisting of hydrogen and $C_1$-$C_3$ alkyl.
17. The compound of claim 1, wherein R⁵ and R⁶ are hydrogen, R³ is $C_1$-$C_3$ alkyl and R⁴ is selected from the group consisting of hydrogen and $C_1$-$C_3$ alkyl.
18. The compound of claim 1, wherein the $OCHF_2$-radical in formula I is located on the benzene ring in the ortho-position with respect to the sulfonyl group.
19. The compound of claim 1, wherein the $OCHF_2$-radical in formula I is located on the benzene ring in the meta-position with respect to the sulfonyl group.
20. The compound of claim 1, wherein the $OCHF_2$-radical in formula I is located on the benzene ring in the para-position with respect to the sulfonyl group.
21. The compound of claim 1, selected from the group consisting of:
N-(3-[1,4]diazepan-1-yl-4-methoxy-phenyl)-3-difluoromethoxy-benzenesulfonamide;
3-difluoromethoxy-N-[4-methoxy-3-(4-methyl-[1,4]diazepan-1-yl)-phenyl]-benzenesulfonamide;
N-(3-[1,4]diazepan-1-yl-4-methoxy-phenyl)-2-difluoromethoxy-benzenesulfonamide;
2-difluoromethoxy-N-[4-methoxy-3-(4-methyl-[1,4]diazepan-1-yl)-phenyl]-benzenesulfonamide;
N-(3-[1,4]diazepan-1-yl-4-methyl-phenyl)-2-difluoromethoxy-benzenesulfonamide;
N-(3-[1,4]diazepan-1-yl-4-methyl-phenyl)-3-difluoromethoxy-N-methyl-benzenesulfonamide;
N-(3-[1,4]diazepan-1-yl-4-methyl-phenyl)-3-difluoromethoxy-benzenesulfonamide; and
2-difluoromethoxy-N-[4-methyl-3-(4-methyl-[1,4]diazepan-1-yl)-phenyl]-benzenesulfonamide;
and physiologically tolerated acid addition salts and the N-oxides thereof.

22. A method for treating obesity, said method comprising administering to a subject in need thereof an effective amount of a compound of formula I or I'

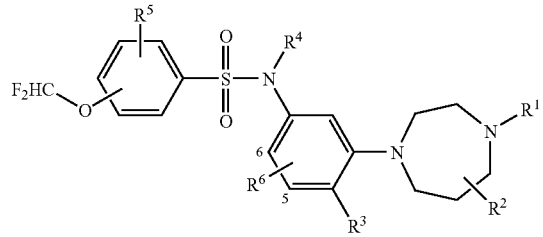

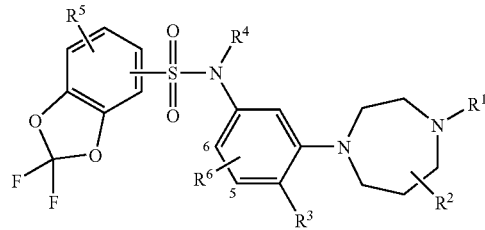

wherein
R¹ is hydrogen or methyl;
R² is hydrogen or methyl;
R³ hydrogen, $C_1$-$C_3$ alkyl, halogen, $C_1$-$C_3$ alkoxy, fluorinated $C_1$-$C_3$ alkyl or fluorinated $C_1$-$C_3$ alkoxy;
R⁴ is hydrogen, $C_1$-$C_4$ alkyl, $C_3$-$C_4$ cycloalkyl, $C_3$-$C_4$ cycloalkylmethyl or fluorinated $C_1$-$C_4$ alkyl;
R⁵ is hydrogen, fluorine, chlorine, $C_1$-$C_4$ alkyl, fluorinated $C_1$-$C_4$ alkyl, $C_1$-$C_4$ alkoxy or fluorinated $C_1$-$C_4$ alkoxy; and
R⁶ is hydrogen, fluorine or chlorine;
wherein R² is positioned vicinal to the radical R¹;
and physiologically tolerated acid addition salts and the N-oxides thereof.

23. A method for treating a cognitive dysfunction associated with Alzheimer's disease or schizophrenia, said method comprising administering to a subject in need thereof an effective amount of a compound of formula I or I'

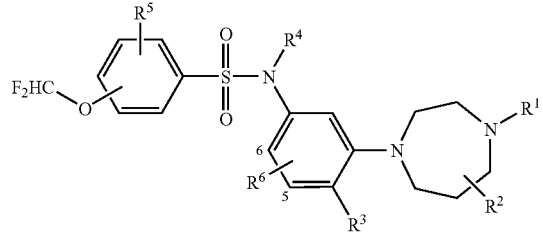

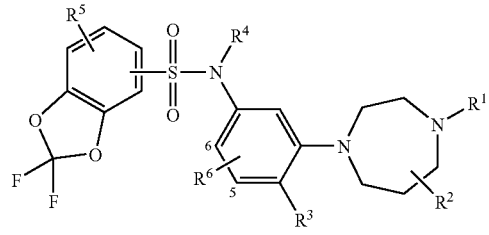

wherein
R¹ is hydrogen or methyl;
R² is hydrogen or methyl;

$R^3$ hydrogen, $C_1$-$C_3$ alkyl, halogen, $C_1$-$C_3$ alkoxy, fluorinated $C_1$-$C_3$ alkyl or fluorinated $C_1$-$C_3$ alkoxy;

$R^4$ is hydrogen, $C_1$-$C_4$ alkyl, $C_3$-$C_4$ cycloalkyl, $C_3$-$C_4$ cycloalkylmethyl or fluorinated $C_1$-$C_4$ alkyl;

$R^5$ is hydrogen, fluorine, chlorine, $C_1$-$C_4$ alkyl, fluorinated $C_1$-$C_4$ alkyl, $C_1$-$C_4$ alkoxy or fluorinated $C_1$-$C_4$ alkoxy; and $R^6$ is hydrogen, fluorine or chlorine;

wherein $R^2$ is positioned vicinal to the radical $R^1$;

and physiologically tolerated acid addition salts and the N-oxides thereof.

* * * * *